(12) United States Patent
Koo et al.

(10) Patent No.: US 12,027,275 B2
(45) Date of Patent: Jul. 2, 2024

(54) SYSTEMS AND METHODS FOR ESTIMATING HEMODYNAMIC FORCES ACTING ON PLAQUE AND MONITORING RISK

(71) Applicant: HeartFlow, Inc., Mountain View, CA (US)

(72) Inventors: Bon-Kwon Koo, Seoul (KR); Gilwoo Choi, Mountain View, CA (US); Hyun Jin Kim, San Mateo, CA (US); Charles A. Taylor, Atherton, CA (US)

(73) Assignee: HeartFlow, Inc., Mountain View, CA (US)

( * ) Notice: Subject to any disclaimer, the term of this patent is extended or adjusted under 35 U.S.C. 154(b) by 0 days.

(21) Appl. No.: 18/355,500

(22) Filed: Jul. 20, 2023

(65) Prior Publication Data
US 2023/0360804 A1 Nov. 9, 2023

Related U.S. Application Data

(63) Continuation of application No. 17/933,176, filed on Sep. 19, 2022, now Pat. No. 11,756,690, which is a (Continued)

(51) Int. Cl.
*G16H 50/50* (2018.01)
*A61B 5/02* (2006.01)
(Continued)

(52) U.S. Cl.
CPC ......... *G16H 50/50* (2018.01); *A61B 5/02007* (2013.01); *A61B 5/0215* (2013.01);
(Continued)

(58) Field of Classification Search
CPC ........ G16H 50/50; G16H 50/30; G16H 50/20; A61B 5/02007; A61B 5/0215; A61B 5/026
See application file for complete search history.

(56) References Cited

U.S. PATENT DOCUMENTS 11,482,339 B2  10/2022 Koo et al.
2004/0044269 A1  3/2004 Shibata
(Continued)

FOREIGN PATENT DOCUMENTS

WO   2015095282 A1   6/2015

OTHER PUBLICATIONS

Cardiac stress test https://web.archive.org/web/20150506183831/http://en.wikipedia.org/wiki/Cardiac_stress_test, May 2015, pp. 5.
(Continued)

*Primary Examiner* — Curtis B Odom
(74) *Attorney, Agent, or Firm* — Bookoff McAndrews, PLLC

(57) ABSTRACT

Computer-implemented methods are disclosed for estimating values of hemodynamic forces acting on plaque or lesions. One method includes: receiving one or more patient-specific parameters of at least a portion of a patient's vasculature that is prone to plaque progression, rupture, or erosion; constructing a patient-specific geometric model of at least a portion of a patient's vasculature that is prone to plaque progression, rupture, or erosion, using the received one or more patient-specific parameters; estimating, using one or more processors, the values of hemodynamic forces at one or more points on the patient-specific geometric model, using the patient-specific parameters and geometric model by measuring, deriving, or obtaining one or more of a pressure gradient and a radius gradient; and outputting the estimated values of hemodynamic forces to an electronic storage medium. Systems and computer readable media for executing these methods are also disclosed.

20 Claims, 15 Drawing Sheets

Related U.S. Application Data continuation of application No. 16/875,607, filed on May 15, 2020, now Pat. No. 11,482,339, which is a continuation of application No. 15/201,010, filed on Jul. 1, 2016, now Pat. No. 10,692,608, which is a continuation of application No. 15/199,305, filed on Jun. 30, 2016, now Pat. No. 9,785,748.

(60) Provisional application No. 62/192,314, filed on Jul. 14, 2015.

(51) Int. Cl.
- A61B 5/0215 (2006.01)
- A61B 5/026 (2006.01)
- G16H 50/20 (2018.01)
- G16H 50/30 (2018.01)

(52) U.S. Cl.
CPC ............. *A61B 5/026* (2013.01); *G16H 50/20* (2018.01); *G16H 50/30* (2018.01)

(56) References Cited

U.S. PATENT DOCUMENTS

| | | |
|---|---|---|
| 2007/0010751 A1 | 1/2007 | Amano et al. |
| 2010/0130878 A1 | 5/2010 | Lasso et al. |
| 2010/0249620 A1 | 9/2010 | Cho |
| 2013/0013278 A1 | 1/2013 | Hu |
| 2013/0325359 A1 | 12/2013 | Jarverud et al. |
| 2014/0073969 A1 | 3/2014 | Zou et al. |
| 2014/0073977 A1 | 3/2014 | Grady et al. |
| 2014/0155770 A1 | 6/2014 | Taylor |
| 2015/0073766 A1 | 3/2015 | Hart et al. |
| 2015/0112182 A1 | 4/2015 | Sharma et al. |
| 2016/0148371 A1 | 5/2016 | Itu et al. |
| 2017/0220760 A1 | 8/2017 | Fonte |

OTHER PUBLICATIONS

Filipovic et al. "Hemodynamic Flow Modeling Through an Abdominal Aorta Aneurysm Using Data Mining Tools", IEEE Biomedicine, vol. 15, No. 2, 2011, pp. 180-194.

Fillinger et al. "Prediction of rupture risk in abdominal aortic aneurysm during observation: Wall stress versus diameter", J. Vascular Surgery, 2003, pp. 724-732.

International Search Report and the Written Opinion received in related PCT US/2016/042093 dated Sep. 22, 2016 (12 pages).

Jerrold T. Bushberg, "The essential physics of medical imaging," 2012, Lippicott Williams & Wilkins, p. 342.

Wei Zhang et al., "Effect of surrounding tissue on vessel fluid and solid mechanics," 2004, Journal of Biomechanical engineering, vol. 126, Dec. 2004, pp. 760-769.

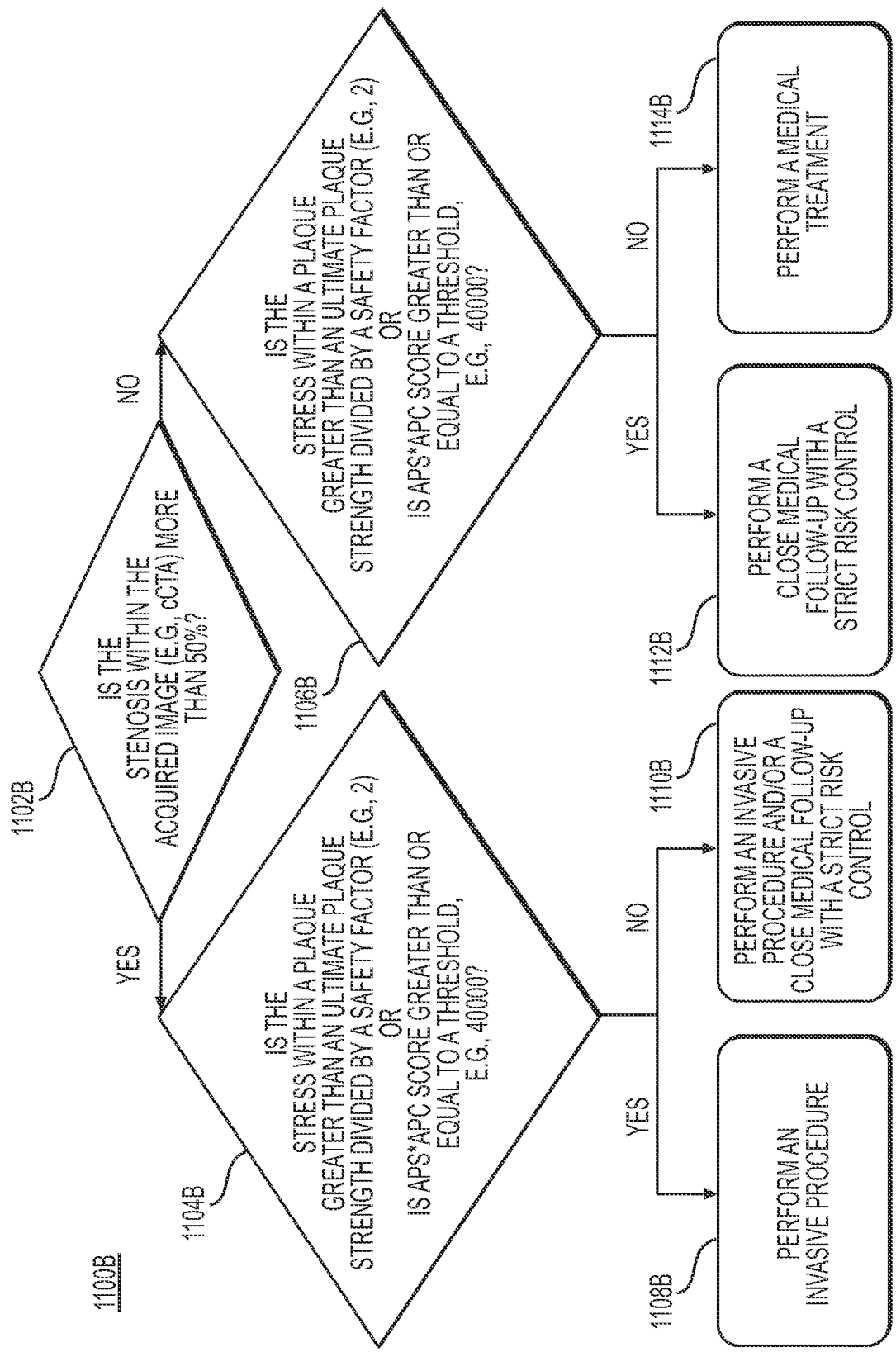

SYSTEMS AND METHODS FOR ESTIMATING HEMODYNAMIC FORCES ACTING ON PLAQUE AND MONITORING RISK

RELATED APPLICATION(S)

This application is a continuation of U.S. application Ser. No. 17/933,176, filed Sep. 19, 2022, which is a continuation of U.S. application Ser. No. 16/875,607, filed May 15, 2020, now U.S. Pat. No. 11,482,339, which is a continuation of U.S. application Ser. No. 15/201,010, filed Jul. 1, 2016, now U.S. Pat. No. 10,692,608, which is a continuation of U.S. application Ser. No. 15/199,305, filed Jun. 30, 2016, now U.S. Pat. No. 9,785,748, which claims priority to U.S. Provisional Application No. 62/192,314, filed Jul. 14, 2015, the entire disclosures of which are hereby incorporated herein by reference in their entireties.

FIELD OF THE DISCLOSURE

Various embodiments of the present disclosure relate generally to medical imaging, health risk monitoring, and related methods. More specifically, particular embodiments of the present disclosure relate to systems and methods for estimating hemodynamic forces acting on plaque, and monitoring risk.

BACKGROUND

Atherosclerosis is a specific form of arteriosclerosis, caused by thickening artery walls and plaque formation. Hemodynamic forces, including wall shear stress (WSS) and axial plaque stress (APS), may affect the pathogenesis of coronary atherosclerosis. In particular, wall shear stress may affect the progression of coronary plaques, while axial plaque stress (APS), which is the axial component of traction, may influence the risk of plaque rupture. Since these hemodynamic parameters may have unique characteristics in lesions as compared to conventional metrics, e.g., lesion severity or fractional flow reserve (FFR), considering these hemodynamic forces in the clinical decision-making process may improve the risk stratification of plaques and ultimately help patient care.

Axial plaque stress may correlate to radius gradient in a patient's vascular geometry. Radius gradient may incorporate clinically relevant geometric parameters, including lesion length, minimum lumen area, and stenosis severity. Thus, a desire exists for a method of providing a patient-specific evaluation of axial plaque stress and radius gradient to provide improved treatment strategies for vascular disease. Furthermore, a desire exists for a method of monitoring hemodynamic parameters (e.g., axial plaque stress, radius gradient, etc.) for discharged outpatients in order to provide continued personalized care.

SUMMARY

The foregoing general description and the following detailed description are exemplary and explanatory only and are not restrictive of the disclosure. According to certain aspects of the present disclosure, systems and methods are disclosed for estimating values of hemodynamic forces acting on plaque or lesions.

One method includes: receiving one or more patient-specific parameters of at least a portion of a patient's vasculature that is prone to plaque progression, rupture, or erosion; constructing a patient-specific geometric model of at least a portion of a patient's vasculature that is prone to plaque progression, rupture, or erosion, using the received one or more patient-specific parameters; estimating, using one or more processors, the values of hemodynamic forces at one or more points on the patient-specific geometric model, using the patient-specific parameters and geometric model by measuring, deriving, or obtaining one or more of a pressure gradient and a radius gradient; and outputting the estimated values of hemodynamic forces to an electronic storage medium.

In accordance with another embodiment, a system for estimating values of hemodynamic forces acting on plaque or lesions comprises: a data storage device storing instructions for estimating values of hemodynamic forces; and a processor configured for: receiving one or more patient-specific parameters of at least a portion of a patient's vasculature that is prone to plaque progression, rupture, or erosion; constructing a patient-specific geometric model of at least a portion of a patient's vasculature that is prone to plaque progression, rupture, or erosion, using the received one or more patient-specific parameters; estimating, using one or more processors, the values of hemodynamic forces at one or more points on the patient-specific geometric model, using the patient-specific parameters and geometric model by measuring, deriving, or obtaining one or more of a pressure gradient and a radius gradient; and outputting the estimated values of hemodynamic forces to an electronic storage medium.

In accordance with another embodiment, a non-transitory computer readable medium for use on a computer system containing computer-executable programming instructions for performing a method of estimating values of hemodynamic forces acting on plaque or lesions, the method comprising: receiving one or more patient-specific parameters of at least a portion of a patient's vasculature that is prone to plaque progression, rupture, or erosion; constructing a patient-specific geometric model of at least a portion of a patient's vasculature that is prone to plaque progression, rupture, or erosion, using the received one or more patient-specific parameters; estimating, using one or more processors, the values of hemodynamic forces at one or more points on the patient-specific geometric model, using the patient-specific parameters and geometric model by measuring, deriving, or obtaining one or more of a pressure gradient and a radius gradient; and outputting the estimated values of hemodynamic forces to an electronic storage medium.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

FIG. 5 may depict an exemplary method of performing step 302 of method 300 in FIG. 3 and/or step 402 of method 400 in FIG. 4.

FIG. 6 may depict an exemplary method of performing step 306 of method 300 in FIG. 3 and/or step 408 of method 400 in FIG. 4.

FIG. 7 may depict an exemplary method for training a machine learning algorithm for estimating values of hemodynamic forces, using non-invasive imaging and computational fluid dynamics.

FIG. 8 may depict an exemplary method of applying a trained machine learning algorithm to estimate values of hemodynamic forces, using a non-invasively acquired geometric model of a target patient.

FIG. 9 may depict an exemplary method of applying a trained machine learning algorithm to estimate values of hemodynamic forces, using an invasively acquired geometric model of a target patient.

FIG. 10 may depict an exemplary method of performing steps 710 and 712 of method 700 in FIG. 7, step 808 of method 800 in FIG. 8, and/or step 908 of method 900 in FIG. 9.

FIGS. 11A and 11B are block diagrams of exemplary methods, 1100A and 1100B, respectively, for using the estimated values of hemodynamic forces to monitor risk and make appropriate clinical decisions, according to an exemplary embodiment of the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Atherosclerosis is a specific form of arteriosclerosis, caused by thickening artery walls and plaque formation. Biomechanical and/or hemodynamic forces, may affect or indicate the pathogenesis of coronary atherosclerosis. For purposes of the disclosure, biomechanical and/or hemodynamic characteristics, forces, or parameters may include, but are not limited to, the traction, traction force, pressure, pressure gradient, wall shear stress, axial plaque stress, radius gradient, and/or flow fractional reserve (FFR). In particular, wall shear stress may affect the progression of coronary plaques, while axial plaque stress (APS), which may be the axial component of traction, may influence the risk of plaque rupture. Axial plaque stress may correlate to radius gradient in a patient's vascular geometry. Radius gradient may incorporate clinically relevant geometric parameters, including lesion length, minimum lumen area, and stenosis severity. Since certain hemodynamic forces (e.g. wall shear stress, axial plaque stress, radius gradient, etc.) may have unique characteristics in lesions as compared to traditional metrics to characterize blood flow, e.g., lesion severity or fractional flow reserve (FFR), the consideration of certain hemodynamic forces, including, but not limited to, the wall shear stress, axial plaque stress, and radius gradient, in the clinical decision-making process may improve the risk stratification of plaques and ultimately help patient care.

The embodiments of the present disclosure may provide a patient-specific evaluation of axial plaque stress and radius gradient to identify lesions or plaques exposed to high hemodynamic forces, using invasive and noninvasive imaging methods. Such identification may provide improved treatment strategies for vascular disease. In certain embodiments, the disclosed system and method may provide an evaluation of axial plaque stress and radius gradient to show why plaque rupture may occur in a downstream segment of a vasculature as well as an upstream segment of a vasculature. Analyzing axial plaque stress with radius gradient may further show why plaques may be more likely to rupture in short focal lesions rather than diffuse ones.

Furthermore, embodiments of the present disclosure may provide systems and methods of monitoring hemodynamic forces (e.g., axial plaque stress, radius gradient, etc.) for discharged outpatients through mobile devices such as a smart-phone or smart-watch in order to provide continued personalized care.

Figure 1:
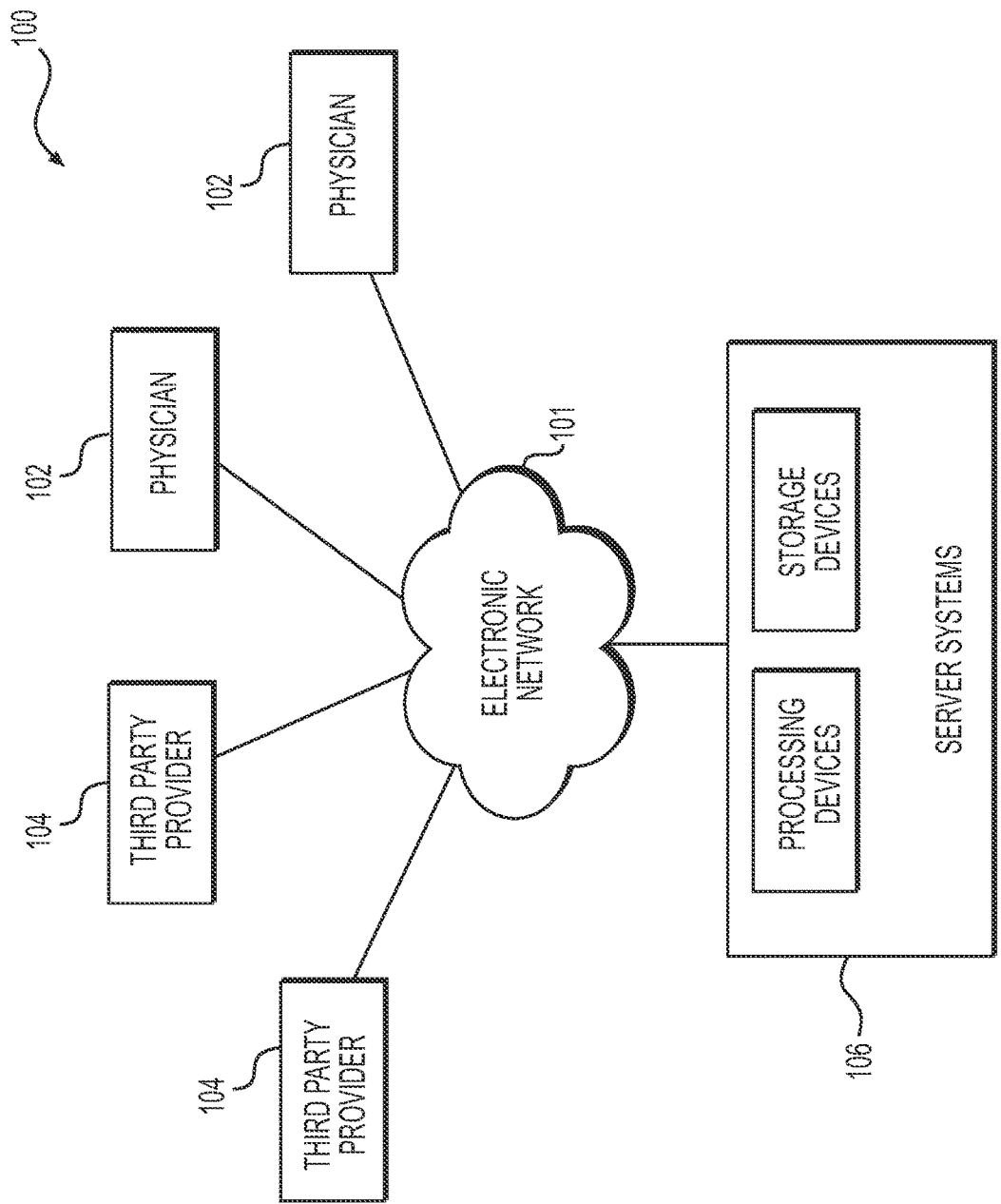
FIG. 1 is a block diagram of an exemplary system and network for estimating hemodynamic forces acting on plaque and monitoring risk, according to an exemplary embodiment of the present disclosure.

Referring now to the figures, FIG. 1 depicts a block diagram of an exemplary system 100 and network for estimating values of hemodynamic forces acting on plaque and monitoring patient risk, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. For purposes of the disclosure, a "patient" may refer to any individual or person for whom diagnosis or treatment analysis is being performed, hemodynamic forces are being estimated, or risks associated with hemodynamic characteristics are being monitored, or any individual or person associated with the diagnosis or treatment of cardiovascular diseases or conditions, or any individual or person associated with the analysis of hemodynamic characteristics of one or more individuals. The physicians 102 and/or third party providers 104 may also obtain any combination of patient-specific parameters, including patient characteristics (e.g., age, medical history, etc.) and physiological characteristics (e.g., blood pressure, blood viscosity, patient activity or exercise level, etc.). Physicians 102 and/or third party providers 104 may transmit the anatomical images and/or patient-specific parameters to server systems 106 over the electronic network 101. Server systems 106 may include storage devices for storing images and data received from physicians 102 and/or third party providers 104. Server systems 106 may also include processing devices for processing images and data stored in the storage devices.

Figure 2A:
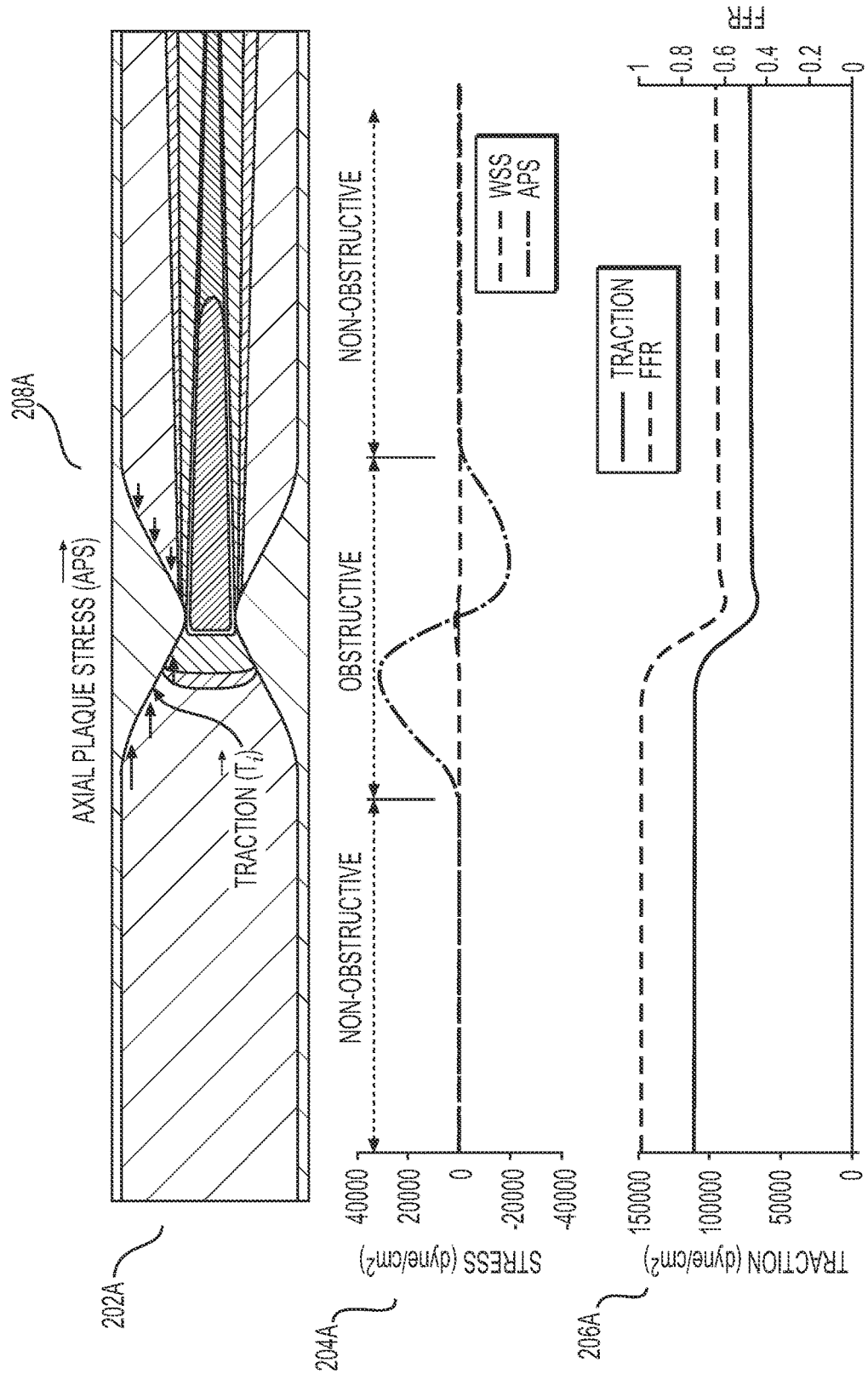
FIG. 2A depicts pictorial and graphical diagrams of hemodynamic forces acting on plaque, according to an exemplary embodiment of the present disclosure.

FIG. 2A depicts pictorial and graphical diagrams of hemodynamic forces acting on plaque, according to an exemplary embodiment. Specifically, FIG. 2A depicts a longitudinal section of vessel 202A, with a portion of the length of the vessel being afflicted by an obstruction 208A, and graphs indicating fluctuations in stress values 204A and traction values 206A along the length vessel 202A. The obstructive area 208A of the vessel may be caused by a plaque and/or lesion. The traction may be defined as the total force per area acting on plaques or luminal surfaces. As depicted in the longitudinal section of a vessel 202A, the axial plaque stress (APS) may be defined as a projection of traction onto the centerline of a vessel. Wall shear stress (WSS) may be defined as the tangential component of traction. As depicted in 204A, a change in axial plaque stress and, to a lesser degree, a change in the wall shear stress, may occur near the obstructive area 208A, characterizing an elevation of hemodynamic stress near a plaque or lesion. As depicted in 206A, the traction, and fractional flow reserve may decrease along a vessel length, around and/or downstream from an obstructive area that may be caused by a plaque or lesion. Thus, hemodynamic characteristics (e.g., axial plaque stress) may uniquely characterize obstructive segments of vessels and the present disclosure may be helpful in assessing the future risk of plaque rupture and/or to determine treatment strategy for patients with coronary artery disease.

Figure 2B:
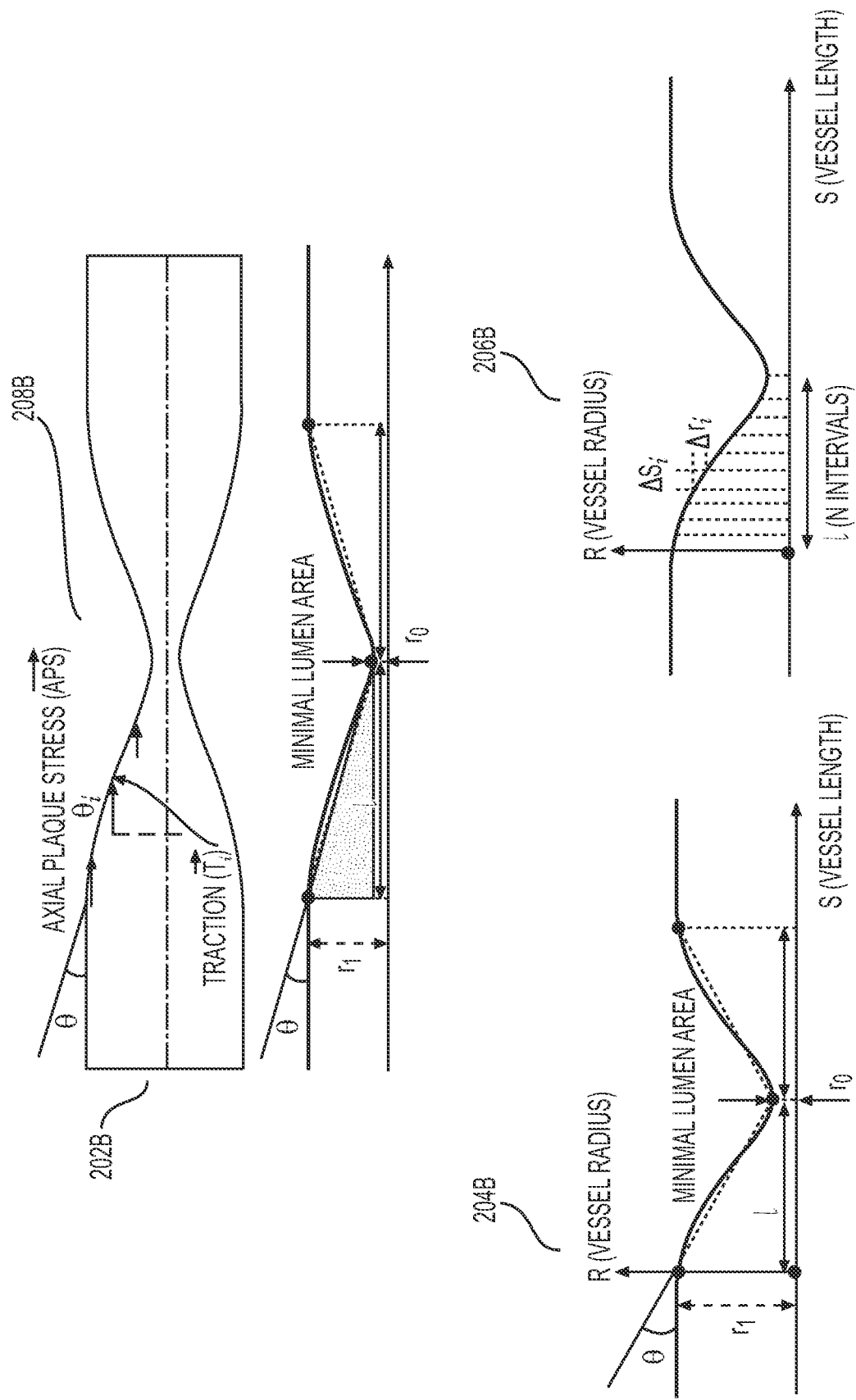
FIG. 2B depicts graphical diagrams and equations illustrating the relationship between hemodynamic forces acting on plaque, according to an exemplary embodiment of the present disclosure.

FIG. 2B depicts graphical diagrams illustrating the relationship between hemodynamic forces acting on plaque, according to an exemplary embodiment of the present disclosure. Specifically, FIG. 2B depicts a longitudinal section of a vessel 202B, with a portion of the length of the vessel being afflicted by an obstruction 208B, a graphs depicting methods for computing an approximated or analytic values of the radius gradient (RG), 204B and 206B, respectively, with radius gradient (RG) values to be used in the computation of the axial plaque stress value. In one embodiment, an approximated value of the radius gradient, RG, may be computed as follows:

$$RG = \frac{r_1 - r_0}{l},$$

where $r_1$ is the maximum radius and $r_2$ is the minimum radius over a vessel of length l, as depicted in 204B. An analytic value of the radius gradient, analytic RG, may be computed as follows:

$$\text{analytic } RG = \frac{1}{N}\sum_{i=1}^{N}\frac{\Delta r_i}{\Delta s_i},$$

where N is the number of intervals over length, l of a vessel, $\Delta r_i$ is the change in radius over a change in interval, $\Delta S_i$, as depicted in 206B.

The obstructive area 208B of the vessel may be caused by a plaque and/or lesion. The axial plaque stress (APS), which may be defined as the projection of traction onto the centerline of a vessel, may be computed by multiplying the pressure times the radius gradient, with the radius gradient being the luminal radius change over the length of a vessel and/or vessel segment. For example, an axial plaque stress upstream of the obstruction, $\overrightarrow{APS}_{upstream}$, may be computed as follows:

$$\overrightarrow{APS}_{upstream} = \sum \overrightarrow{T}_i \sin\theta_i \approx \text{Pressure}\frac{r_1 - r_0}{\sqrt{l^2 + (r_1 - r_0)^2}}$$

$$= \text{Pressure}\frac{\frac{r_1 - r_0}{l}}{\sqrt{1 + \left(\frac{r_1 - r_0}{l}\right)^2}} \approx \text{Pressure}\frac{r_1 - r_0}{l}$$

$$= \text{Pressure} \cdot \text{Radius Gradient}$$

where $\overrightarrow{T}_i$ is the traction, r is the vessel radius, l is the length of the vessel under analysis, and θ is the angle of the obstruction with respect to the centerline of the vessel, as depicted in 202B.

Figure 3:
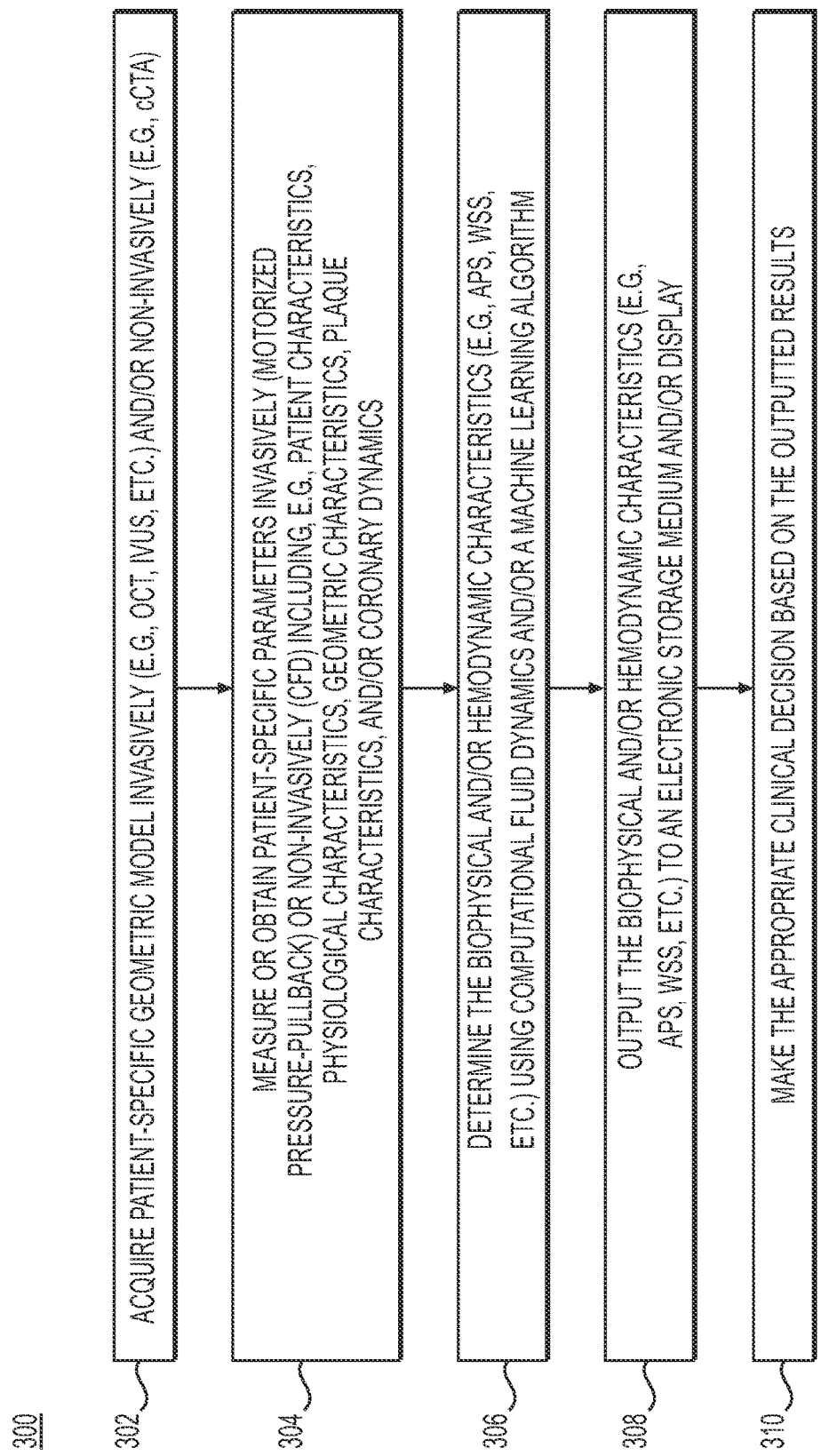
FIG. 3 is a block diagram of a general method of estimating the values of hemodynamic forces acting on plaque and monitoring risk, according to an exemplary embodiment of the present disclosure.
Figure 4:
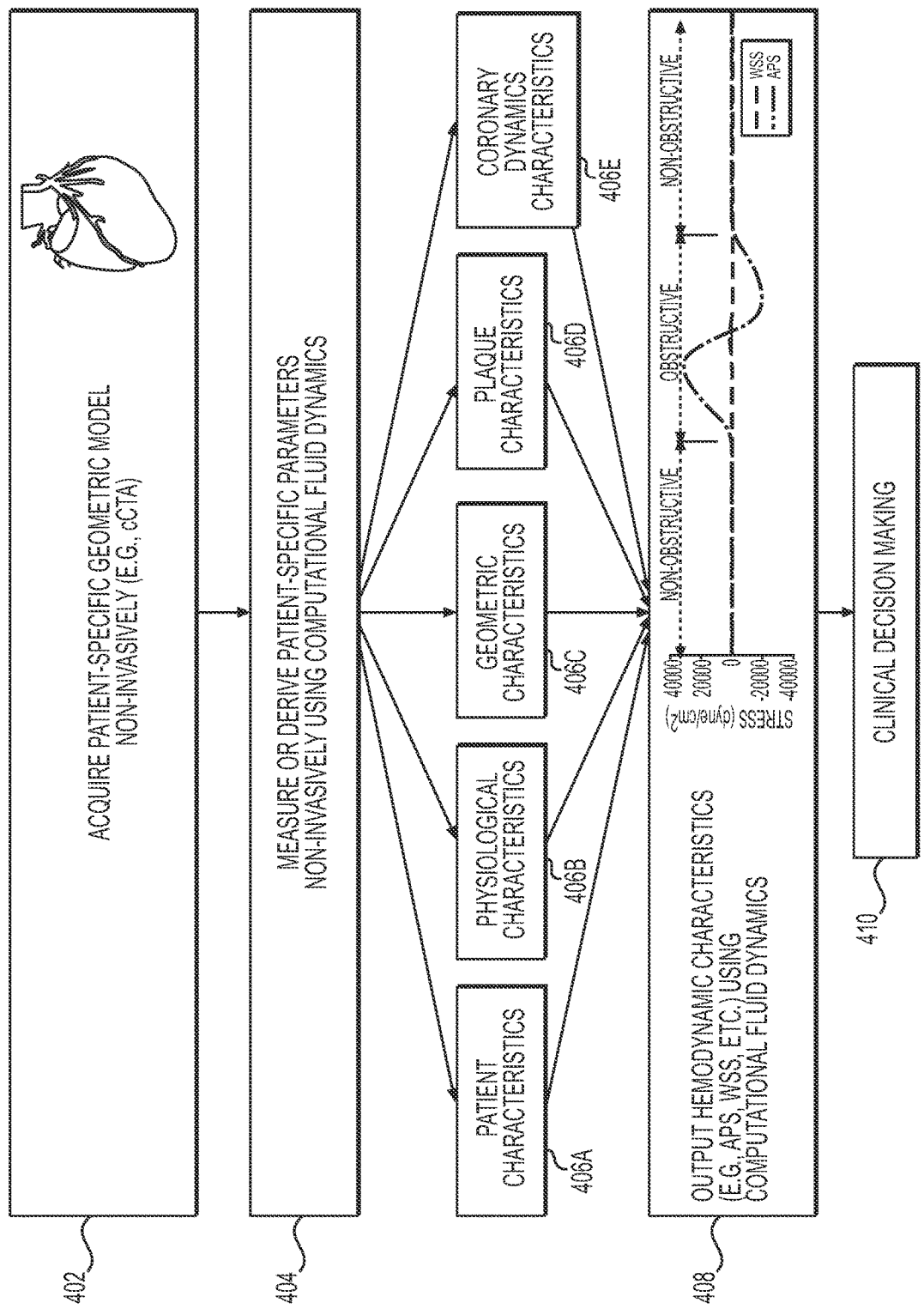
FIG. 4 is a block diagram of an exemplary method of estimating the values of hemodynamic forces acting on plaque and monitoring risk, using non-invasive imaging and computational fluid dynamics, according to an exemplary embodiment of the present disclosure.
Figure 5:
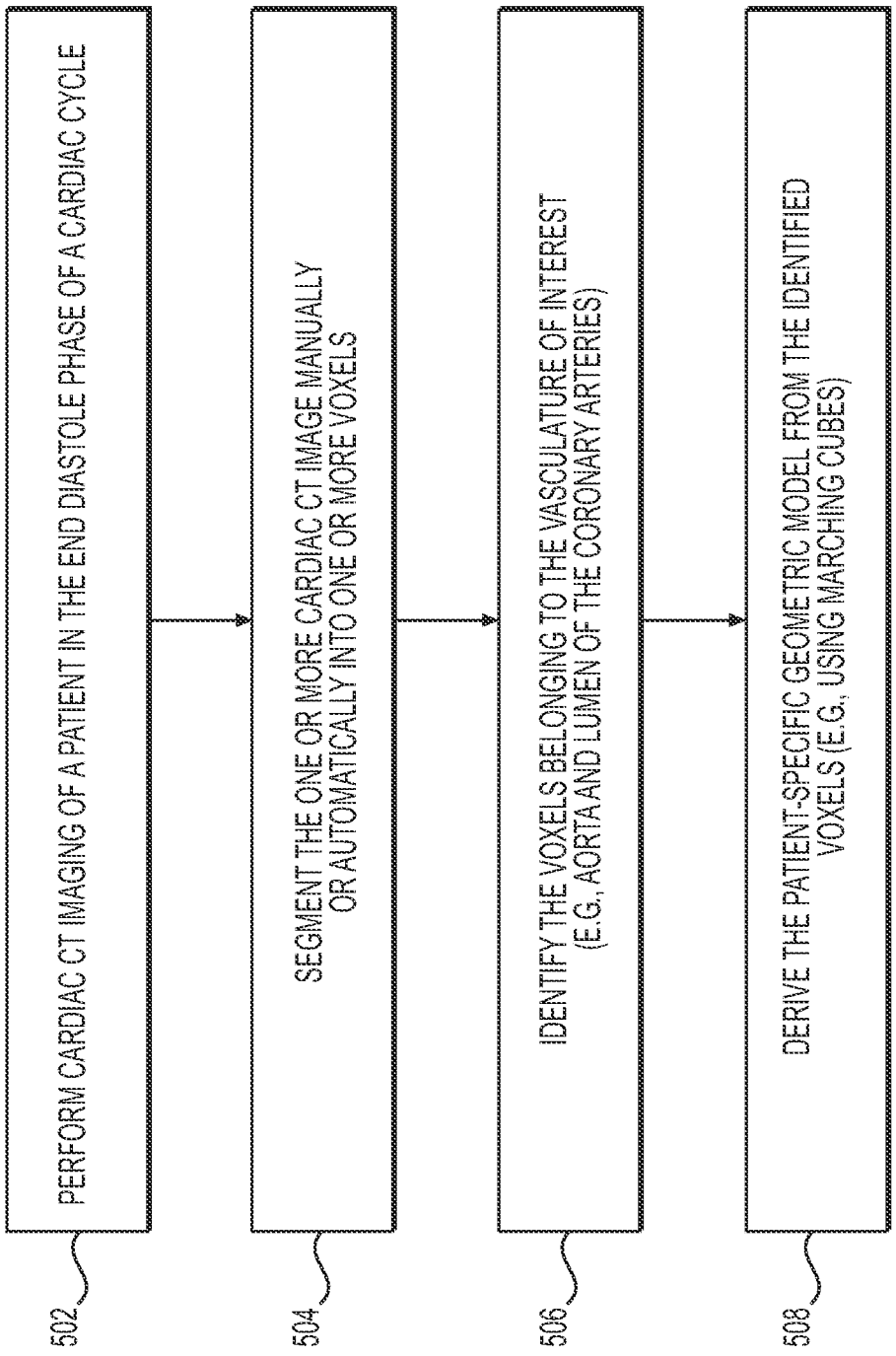
FIG. 5 is a block diagram of an exemplary method of acquiring a patient-specific geometric model non-invasively (e.g., through coronary computerized tomography angiography (cCTA), according to an exemplary embodiment of the present disclosure.
Figure 6:
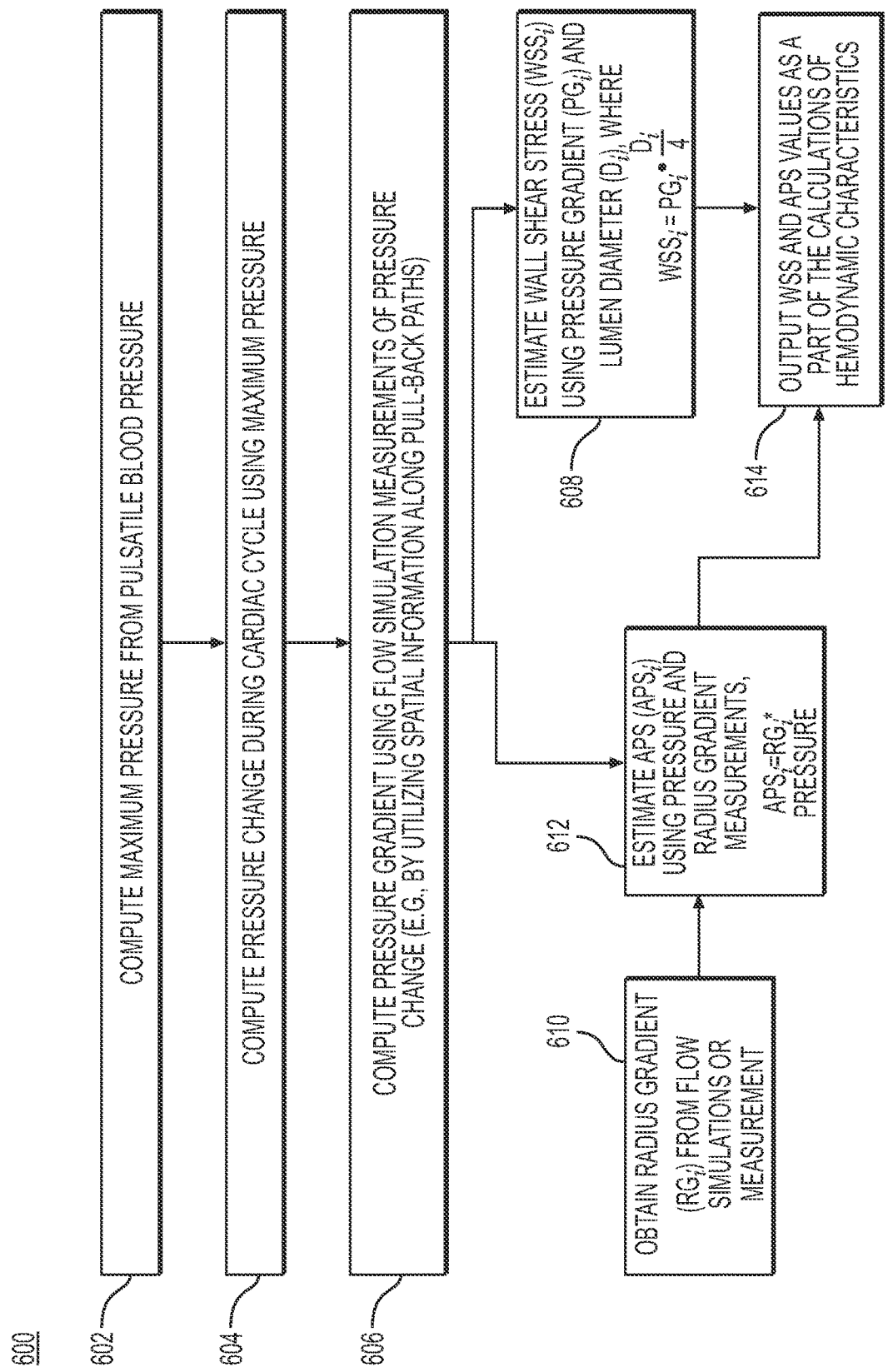
FIG. 6 is a block diagram of an exemplary method of using patient-specific parameters to output the values of hemodynamic forces, using computational fluid dynamics, according to an exemplary embodiment of the present disclosure.
Figure 7:
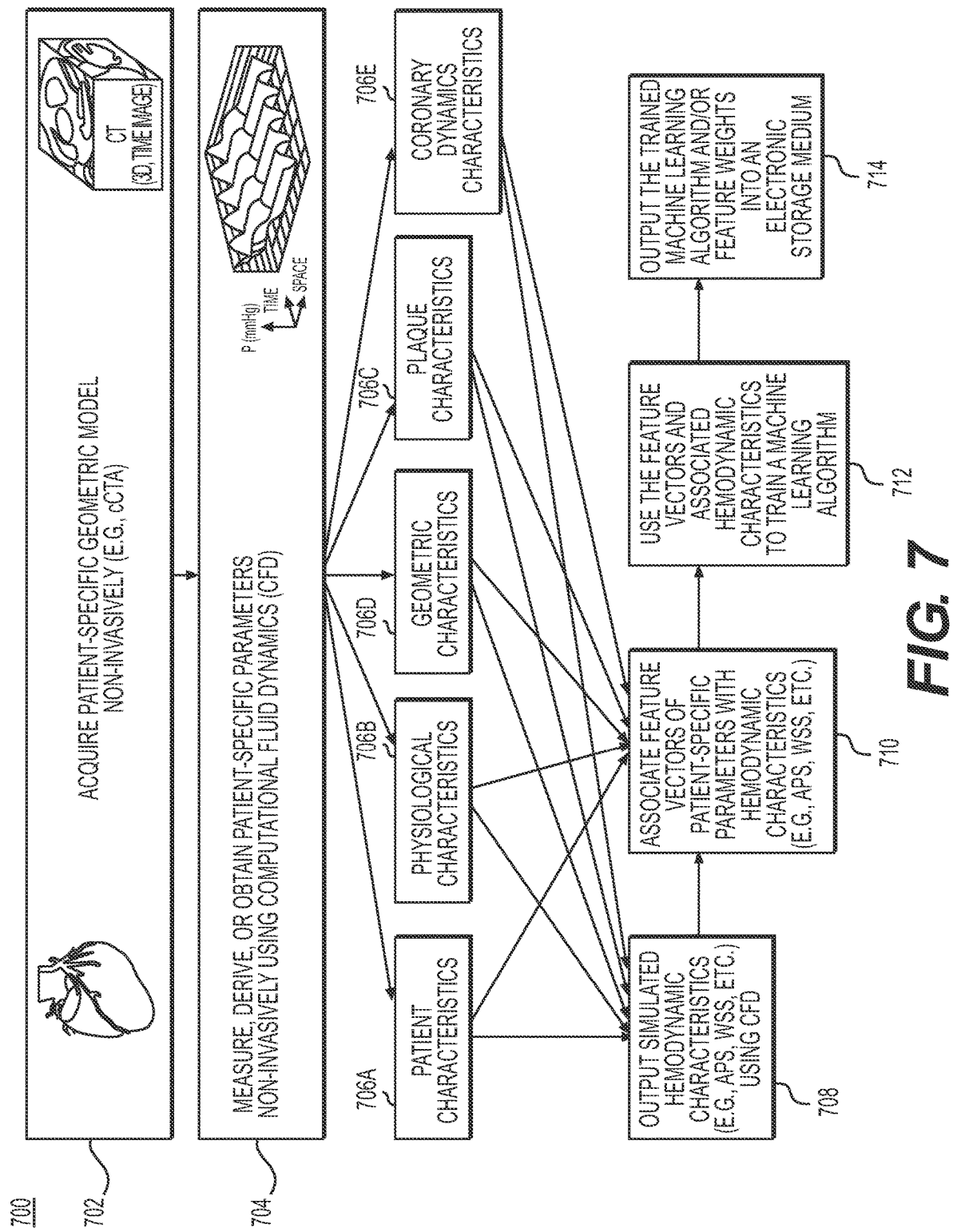
FIGS. 7, 8, and 9 are block diagrams of exemplary methods of estimating the values of hemodynamic forces acting on plaque and monitoring risk, using a machine learning algorithm to estimate values of hemodynamic forces, according to an exemplary embodiment of the present disclosure.
Figure 8:
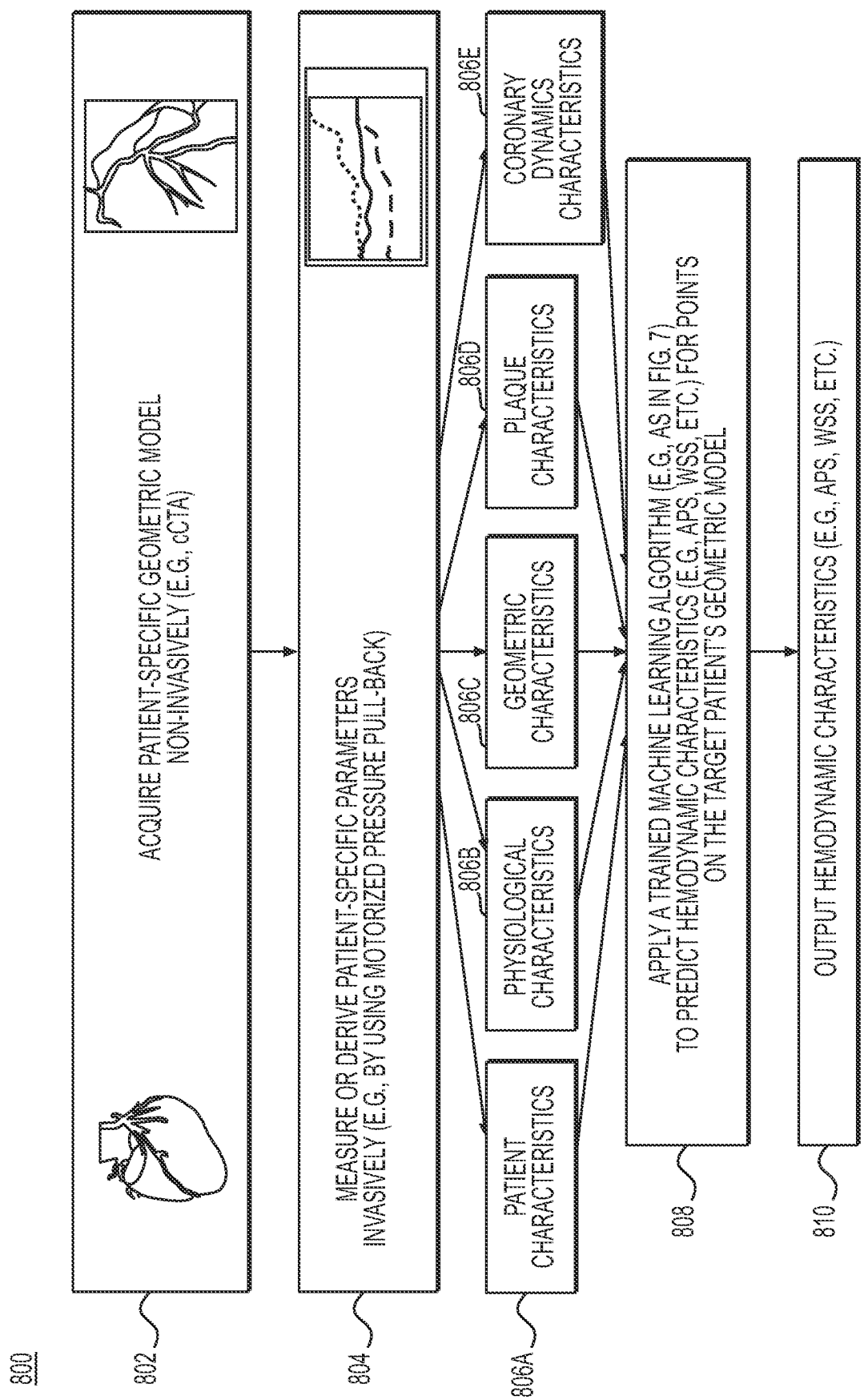
Figure 9:
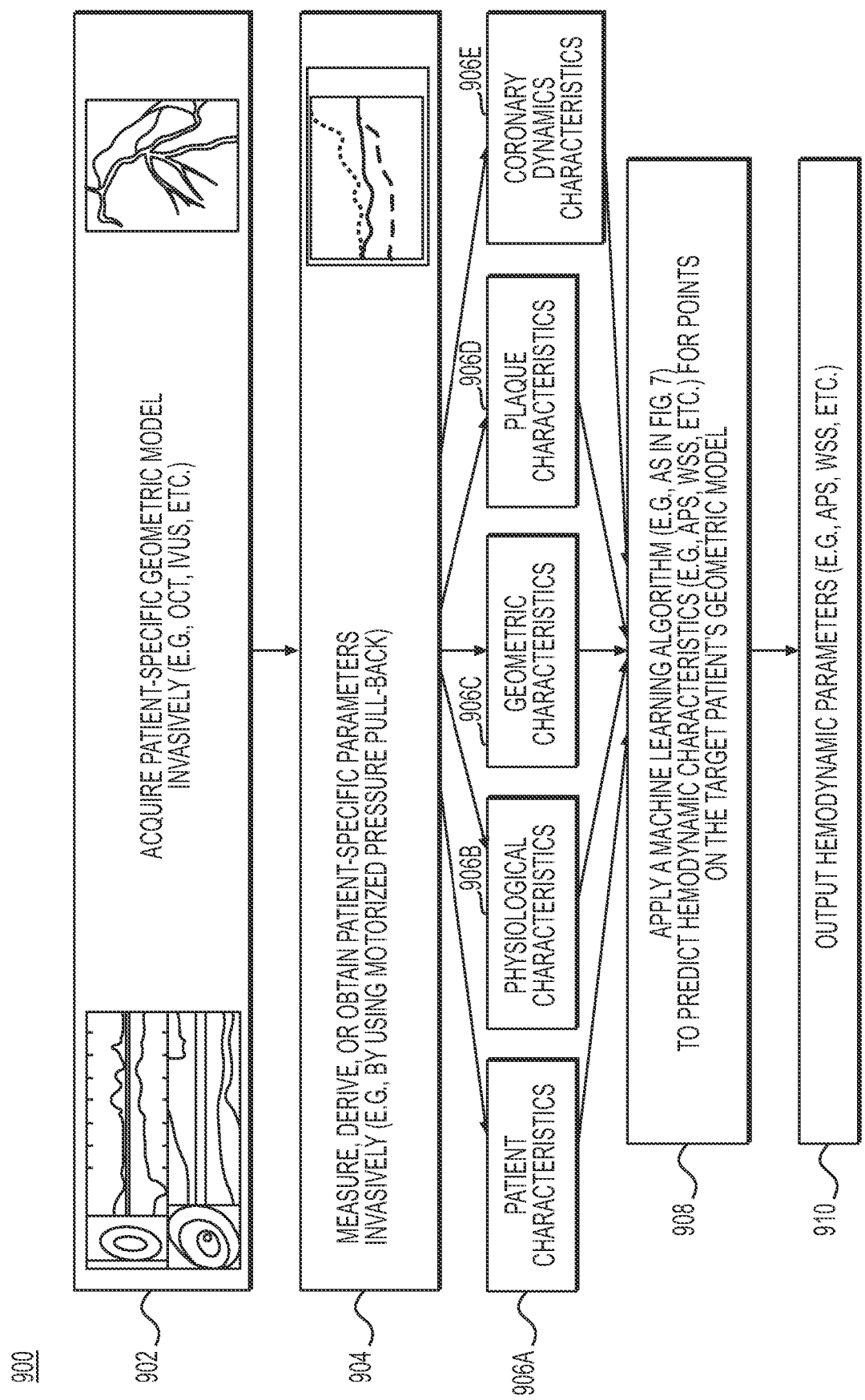
Figure 11A:
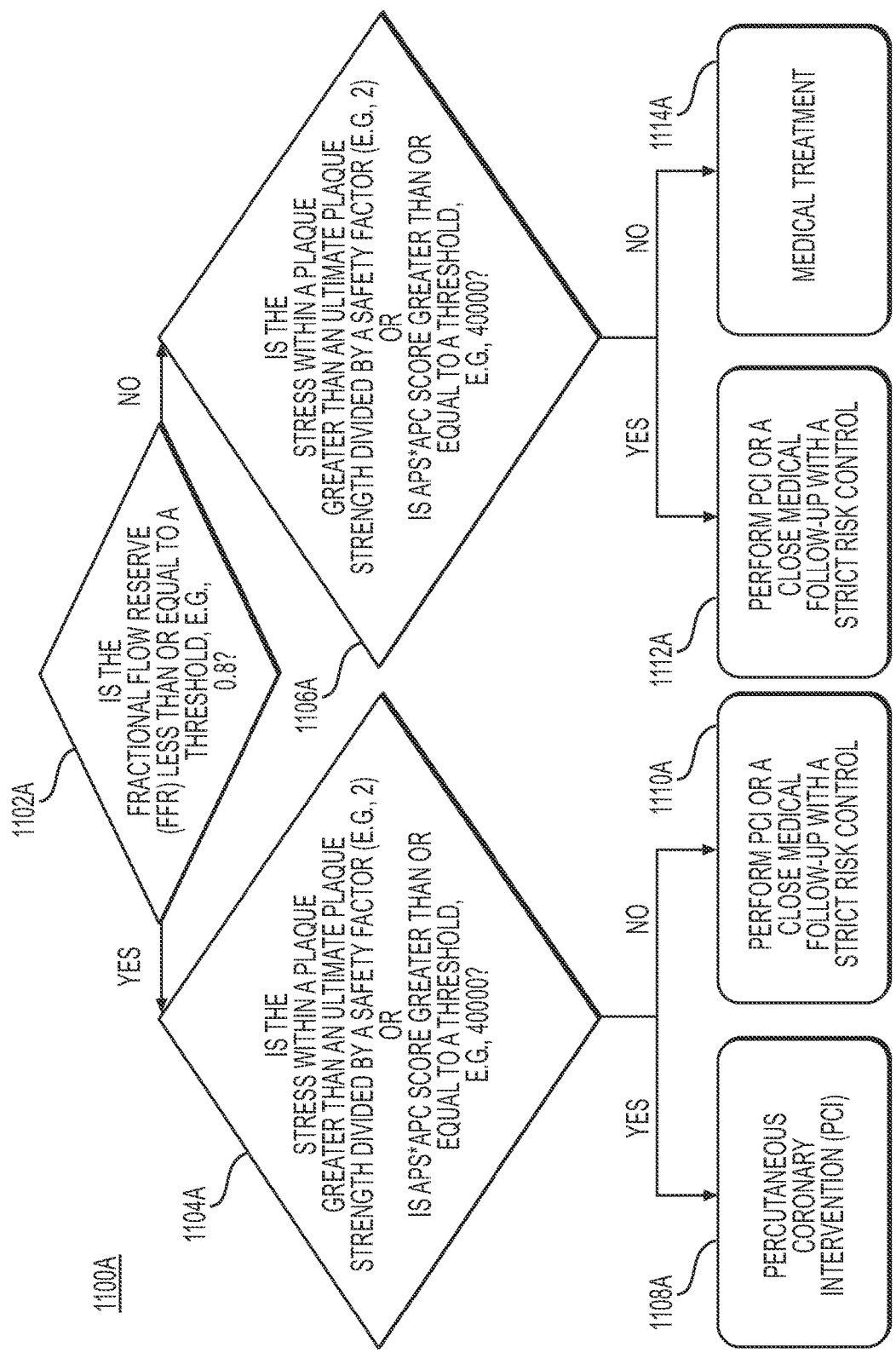
Figure 12:
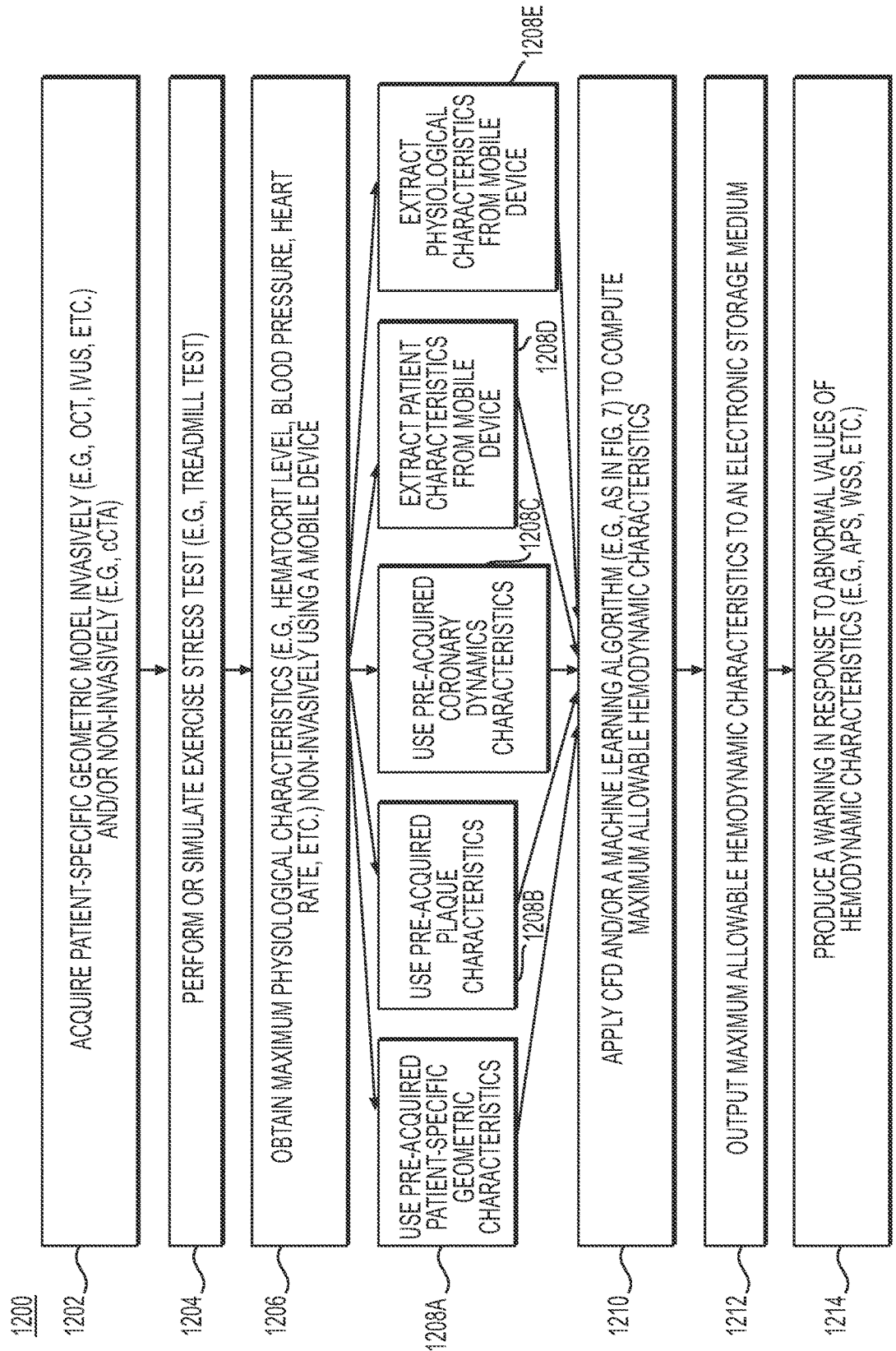
FIG. 12 is a block diagram of exemplary method 1200 for determining an exercise intensity using estimated values of hemodynamic forces based on a simulated or performed exercise and/or stress test, according to an exemplary embodiment of the present disclosure.
Figure 13:
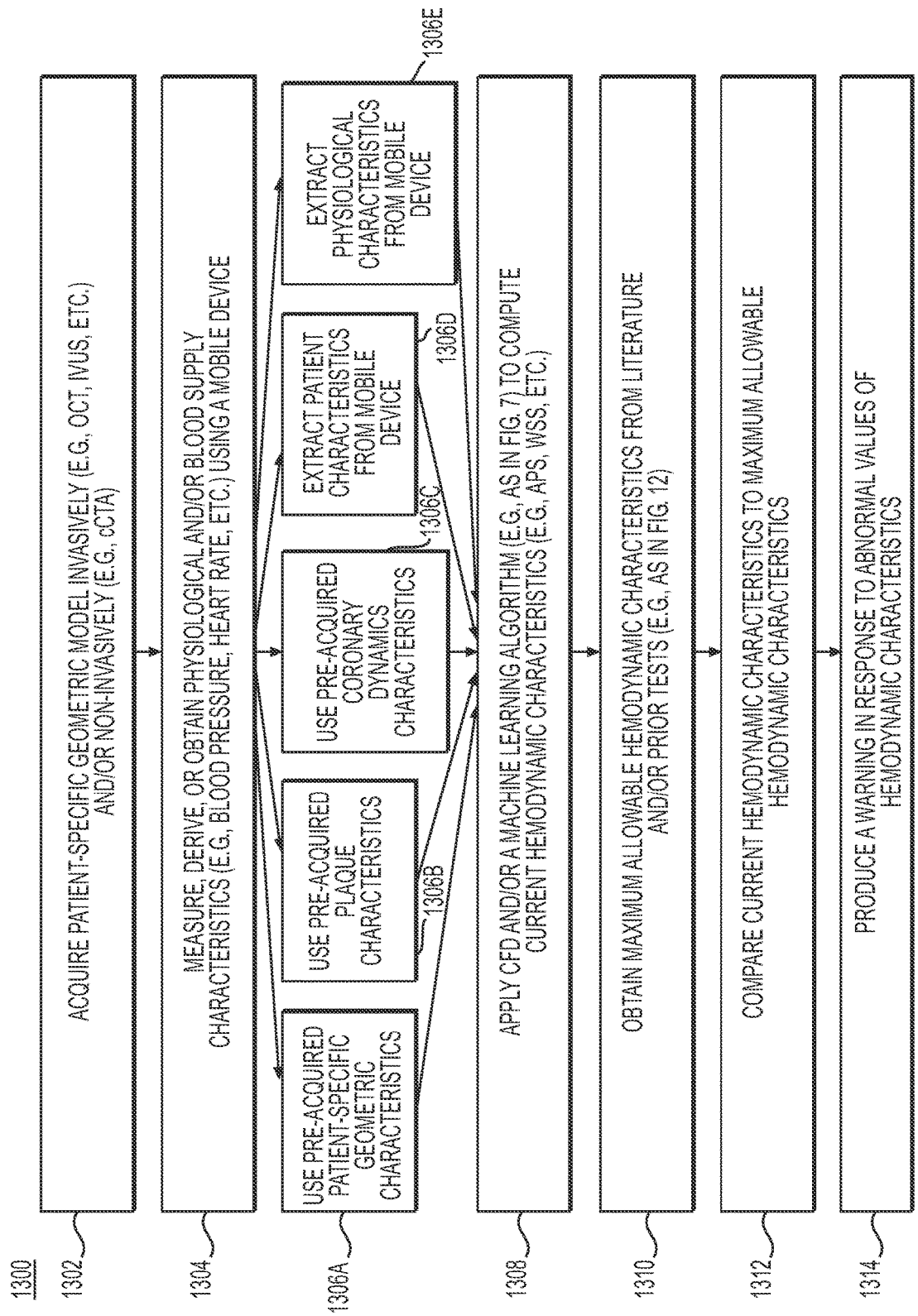
FIG. 13 is a block diagram of exemplary method 1300 for using predetermined exercise intensity (e.g., as in FIG. 12) to monitor risk in patients, according to an exemplary embodiment of the present disclosure.

FIG. 3 depicts a general embodiment of a method 300 for estimating hemodynamic forces acting on plaque and monitoring patient risk. FIGS. 4, 7-9, and 12-13 depict exemplary embodiments of method 300. For example, FIG. 4 depicts an embodiment of a process for estimating values of hemodynamic forces using non-invasive imaging and computational fluid dynamics to obtain hemodynamic characteristics. FIG. 7-9 depict embodiments of estimating values of hemodynamic forces using a machine learning algorithm. FIG. 12-13 depict embodiments of estimating the maximum allowable values of hemodynamic forces and using the estimations to monitor patient risk. FIGS. 5, 6, 8, and 11A-11B depict exemplary steps for method 300 in FIG. 3. For example, FIG. 5 depicts an embodiment for performing step 302 of acquiring a patient-specific geometric model non-invasively (e.g., cCTA). FIG. 6 depicts an embodiment for performing step 306 of outputting the estimated values of hemodynamic characteristics (e.g., APS, WSS, etc.) using computational fluid dynamics. FIG. 8 depicts another embodiment for performing step 306, outputting estimated values of hemodynamic characteristics (e.g., APS, WSS, etc.) using a machine learning algorithm. FIGS. 11A-11B depict an embodiment for performing step 308 of making appropriate clinical decisions based on the saved hemodynamic characteristics.

FIG. 3 is a block diagram of an exemplary method 300 of estimating hemodynamic forces acting on plaque and monitoring patient risk, according to an exemplary embodiment. The method of FIG. 3 may be performed by server systems 106, based on information, images, and data received from physicians 102 and/or third party providers 104 over electronic network 101.

In one embodiment, step 302 may include acquiring a patient-specific geometric model in an electronic storage medium of the server systems 106. Specifically, receiving the patient-specific geometric model may include either generating the patient-specific geometric model at the server system 106, or receiving one over an electronic network (e.g., electronic network 101). In one embodiment, the geometric model may be derived from images of the person acquired invasively or non-invasively via one or more available imaging or scanning modalities. Non-invasive methods for generating the geometric model may include performing cardiac CT imaging of the patient. Invasive methods for generating the geometric model may include performing intravascular ultrasound (IVUS) imaging or optical coherence tomography (OCT) of the target vasculature. The invasively and/or non-invasively acquired image may then be segmented manually or automatically to identify voxels belonging to the vessels and/or lumen of interest. Once the voxels are identified, a geometric model may be derived (e.g., using marching cubes). In one embodiment, the patient-specific geometric model may include a cardiovascular model of a specific person and/or a patient's ascending aorta and coronary artery tree. In another embodiment, the patient-specific geometric model may be of a vascular model other than the cardiovascular model. In one embodiment, the geometric model may be represented as a list of points in space (possibly with a list of neighbors for each point) in which the space may be mapped to spatial units between points (e.g., millimeters).

In one embodiment, step 304 may include measuring, deriving, or obtaining one or more patient-specific parameters invasively or non-invasively in an electronic storage medium of the server systems 106. For purposes of the disclosure, these patient-specific parameters may include, but are not limited to, patient characteristics (e.g., age, gender, etc.), physiological characteristics (e.g., hematocrit level, blood pressure, heart rate, etc.), geometric characteristics (e.g., radius gradient, lumen characteristics, stenosis characteristics, etc.), plaque characteristics (e.g., location of plaque, adverse plaque characteristics score, plaque burden, presence of napkin ring, intensity of plaque, type of plaque, etc.), simplified hemodynamic characteristics (e.g., wall shear stress and axial plaque stress values derived from computational fluid dynamics), and/or coronary dynamics characteristics (e.g., distensibility of coronary artery over cardiac cycle, bifurcation angle change over cardiac cycle, curvature change over cardiac cycle, etc.).

In one embodiment, measuring or deriving patient-specific parameters may also include computing simplified hemodynamics characteristics. In one embodiment, the simplified hemodynamics characteristics (e.g., wall shear stress, axial plaque stress, etc.) may be derived from Hagen-Poiseuille flow assumptions.

Any of the above-mentioned patient-specific parameters (e.g., patient characteristics, physiological characteristics, geometric characteristics, plaque characteristics, simplified hemodynamic characteristics, and/or coronary dynamics characteristics) may be used to measure or derive other patient-specific parameters. In one embodiment, the patient-specific parameters may be used as feature vectors to train and apply machine learning algorithm (e.g., as in step 306).

In one embodiment, step 306 may include determining biophysical and/or hemodynamic characteristics (e.g., axial plaque stress, wall shear stress, etc.) using computational fluid dynamics and/or a machine learning algorithm. In one embodiment, the simplified hemodynamics characteristics (e.g., wall shear stress, axial plaque stress, etc.) may be derived from Hagen-Poiseuille flow assumptions. For example, the wall shear stress may be derived by computing the cross-sectional area at a point i ($A_i$) of the patient's vasculature, computing the effective lumen diameter ($D_i$), where $$D_i = 2\sqrt{\frac{A_i}{\pi}},$$

and estimating the wall shear stress at the point i ($WSS_i$) using a pressure gradient ($PG_i$) computed from a flow simulation or measurements, where $$WSS_i = PG_i \cdot \frac{D_i}{4}.$$

In another example, the axial plaque stress may be derived by computing the radius gradient at a point i ($RG_i$) over an interval (ds), where $$RG_i = (\sqrt{\frac{A_{i+1}}{\pi}} - \sqrt{\frac{A_i}{\pi}})/ds,$$

and estimating APS ($APS_i$) using a radius gradient ($RG_i$) computed from flow simulation or measurements (e.g., as in 206B and 208B of FIG. 2B), where $$APS_i = RG_{analytic} \cdot \text{Pressure} = \frac{1}{N}\sum_1^N RG_i \cdot \text{Pressure}$$

and $APS_i = RG_{ave} \cdot \text{Pressure}$. In one embodiment, the simplified hemodynamic characteristics may be used to compute more accurate hemodynamic characteristics and/or be used as part of a machine learning algorithm to obtain the hemodynamic characteristics for points on the geometric model where the simplified hemodynamic characteristics may not be known.

In one embodiment, step 306 may include using the patient-specific parameters obtained from step 304 (e.g., patient characteristics, physiological characteristics, geometric characteristics, plaque characteristics, simplified hemodynamic characteristics, and/or coronary dynamics characteristics) to form feature vectors to train and apply a machine learning algorithm to determine biomechanical and/or hemodynamic characteristics. For example, for one or more points on the geometric model where simplified hemodynamic characteristics can be calculated using computational fluid dynamics, a feature vector may then be associated with the computed hemodynamic characteristics for the one or more points on the geometric model. The feature vectors and their associated biomechanical and/or hemodynamic characteristics may be used to train a machine learning algorithm that may be stored in an electronic storage medium. The trained machine learning algorithm may be applied to another geometric model using another set of patient-specific parameters to derive biomechanical and/or hemodynamic characteristics for points on the geometric model.

In one embodiment, step 308 may include outputting the estimates of biomechanical and/or hemodynamic characteristics (e.g., wall shear stress, axial plaque stress, radius gradient, etc.) to an electronic storage and/or to a display screen. The estimates of the biomechanical and/or hemodynamic characteristics may be displayed in greyscale or color in 2D or 3D. The estimates of the biophysical and/or hemodynamic characteristics may be overlaid on the geometric model and/or overlaid on an image of the vasculature of interest. For purposes of disclosure, an "electronic storage medium" may include, but is not limited to, a hard drive, network drive, cloud drive, mobile phone, tablet, or the like, whether or not affixed to a display screen.

In one embodiment, step 310 may include making an appropriate clinical decision based on the output biophysical and/or hemodynamic results. In one embodiment, biomechanical and/or hemodynamic characteristics obtained under a given patient physiological state (e.g., rest, hyperemia, varied levels of stress, etc.) may be used to detect abnormal hemodynamic characteristics. In another embodiment, abnormal levels of biomechanical and/or hemodynamic characteristics may activate a warning signal that may be generated from a mobile device to notify patients and/or physicians. In another embodiment, the one or more patient-specific parameters and outputted biomechanical and/or hemodynamic characteristics may be used to compute a risk score, where $$\text{Risk score} = f\left(\frac{\text{Stress within the plaque}}{\text{Ultimate Strength of Plaque}}\right) \approx g(APS, APCscore, etc).$$

In yet another embodiment, a cumulative history of biomechanical and/or hemodynamic results may be used to make the appropriate clinical decisions.

FIG. 4 is a block diagram of an exemplary method of estimating hemodynamic forces acting on plaque and monitoring risk, using non-invasive imaging and computational fluid dynamics to estimate hemodynamic characteristics, according to an exemplary embodiment of the present disclosure. The method of FIG. 4 may be performed by server systems 106, based on information, images, and data received from physicians 102 and/or third party providers 104 over electronic network 101.

In one embodiment, step 402 may include acquiring a patient-specific geometric model non-invasively (e.g., by coronary computerized tomography). This geometrical model may be represented as a list of points in space (possibly with a list of neighbors for each point) in which the space may be mapped to spatial units between points (e.g., millimeters). The geometric model may be generated by performing one or more cardiac or coronary computerized tomography (cCT) imaging of the patient. The one or more cCT images may be segmented manually or automatically to identify voxels belonging to the aorta and the lumen of the coronary arteries. Once the voxels are identified, the geometric model may be derived (e.g., using marching cubes). In one embodiment, the patient-specific geometric model may include a cardiovascular model of a specific person and/or a patient's ascending aorta and coronary artery tree. In another embodiment, the patient-specific geometric model may be of a vascular model other than the cardiovascular model.

In one embodiment, step 404 may include measuring or deriving patient-specific parameters non-invasively (e.g., by using computational fluid dynamics). The measured or derived patient-specific parameters may be stored in an electronic storage medium. These patient-specific parameters may include, but are not limited to patient characteristics (e.g., age, gender, etc.), physiological characteristics (e.g., hematocrit level, blood pressure, heart rate, etc.), geometric characteristics (e.g., radius gradient, lumen characteristics, stenosis characteristics, etc.), plaque characteristics (e.g., location of plaque, adverse plaque characteristics score, plaque burden, presence of napkin ring, intensity of plaque, type of plaque, etc.), simplified hemodynamic characteristics (e.g., wall shear stress and axial plaque stress values derived from computational fluid dynamics), and/or coronary dynamics characteristics (e.g., distensibility of coronary artery over cardiac cycle, bifurcation angle change over cardiac cycle, curvature change over cardiac cycle, etc.). Any of the above-mentioned patient-specific parameters may be used to measure or derive other patient-specific parameters.

Steps 406A, 406B, 406C, 406D, and 406E depict the measured or derived patient characteristics, physiological characteristics, geometric characteristics, plaque characteristics, and coronary dynamics characteristics, respectively. The patient-specific parameters may be stored in an electronic storage medium.

The patient characteristics 406A may include a patient's age, gender, weight, or any other biographical information that may be relevant for the computation of hemodynamic characteristics.

In one embodiment, measuring or deriving physiological characteristics 406B may include, but is not limited to, obtaining a blood pressure profile, EKG, a measurement of heart rate or heart rate change, a pressure gradient along a vessel centerline, and/or blood content profile (e.g., hematocrit level). A pressure gradient may be derived from a simulation or computed over a strip sliced along the vessel centerline (e.g., a 1 mm interval).

In one embodiment, measuring or deriving geometric characteristics 406C may include measuring or deriving lumen characteristics, lesion characteristics, stenosis characteristics, and characteristics of the coronary centerline. The lumen characteristics may include the lumen diameter, the ratio of lumen cross-sectional area with respect to the main ostia (left main or right coronary artery), the degree of tapering in cross-sectional lumen area along the centerline, where centerline points within a certain interval (e.g., twice the diameter of the vessel) may be sampled and a slope of linearly-fitted cross-sectional area may be computed, the irregularity (or circularity) of cross-sectional lumen boundary, characteristics of coronary lumen intensity at a lesion, where the characteristics may include intensity change along the centerline (e.g., using the slope of a linearly fitted intensity variation), the characteristics of surface of coronary geometry at a lesion (e.g., Gaussian maximum, minimum, mean, etc.), and the radius gradient (e.g., by measuring the radius change from the starting or ending point of a lesion point to minimum lumen area location divided by lesion length). The ratio of lumen cross-sectional area with respect to the main ostia (e.g., left main or right coronary artery) may be obtained by measuring the cross-sectional area at the left main ostium, normalizing the cross-sectional area of the left coronary using the left main ostium cross-sectional area, measuring the cross-sectional area at the right coronary artery ostium, and normalizing the cross-sectional area of the right coronary using a right coronary artery ostium area. Stenotic and lesion characteristics may include the degree of stenosis (e.g., by using a Fourier smoothed area graph or kernel regression), the length of a stenotic lesions (e.g., by computing the proximal and distal locations from the stenotic lesion where cross-sectional area is determined), and location of a stenotic lesion (e.g., the distance from stenotic lesion to the main ostia). Characteristics of the coronary centerline (e.g., topology) may include the curvature and tortuosity (non-planarity) of the coronary centerline. The curvature may be obtained by computing the Frenet curvature, κ, where $$\kappa = \frac{|p' \times p''|}{|p'|^3}$$

and p may be a coordinate of centerline parameterized by cumulative arc-length to the starting point, and by computing an inverse of the radius of a circumscribed circle along the centerline points. The tortuosity may be obtained by computing the Frenet torsion, τ, where $$\tau = \frac{(p' \times p'') \cdot p'''}{|p' \times p''|^2},$$

and where p may be a coordinate of a centerline. In one embodiment, measuring or deriving the geometric characteristics 406C may also include obtaining the mass of a myocardium or tissue of interest.

In one embodiment, measuring or deriving plaque characteristics 406D may include obtaining the location of plaque, an adverse plaque characteristics score, the plaque burden (e.g., cap thickness, wall thickness, area, volume, etc.), information on the existence or characteristics of a napkin ring, plaque intensity, and/or plaque type (e.g., calcified, non-calcified, etc.). The location of a plaque may include, but is not limited to, the distance from the plaque to the closest upstream bifurcation point, the angle of bifurcation of the coronary branches if the plaque is located at the bifurcation, the distance from the plaque location to an ostium (left main or right coronary artery), and/or the distance from the plaque location to the nearest downstream and/or upstream bifurcation.

In one embodiment, measuring or deriving coronary dynamics characteristics 406E may include obtaining the distensibility of a coronary artery over a cardiac cycle, the change in a bifurcation angle over a cardiac cycle, and/or the change in curvature of a vessel over a cardiac cycle. The coronary dynamics characteristics may be derived from a multi-phase coronary CT angiography (e.g., diastole and systole).

In one embodiment, step 408 may include outputting hemodynamic characteristics (e.g., axial plaque stress, wall shear stress, etc.) using computational fluid dynamics. In one embodiment, the simplified hemodynamics characteristics (e.g., wall shear stress, axial plaque stress, etc.) may be derived from Hagen-Poiseuille flow assumptions. For example, the wall shear stress may be derived by computing the cross-sectional area at a point i ($A_i$) on a vasculature, computing the effective lumen diameter ($D_i$), where $$D_i = 2\sqrt{\frac{A_i}{\pi}},$$

and estimating the wall shear stress at the point i ($WSS_i$) using a pressure gradient ($PG_i$) computed from a flow simulation or measurements, where $$WSS_i = PG_i \cdot \frac{D_i}{4}.$$

In another example, the axial plaque stress may be derived by computing the radius gradient at a point i ($RG_i$) over an interval (ds), where $$RG_i = (\sqrt{\frac{A_{i+1}}{\pi}} - \sqrt{\frac{A_i}{\pi}})/ds,$$

and estimating the axial plaque stress over a point i, $APS_i$, using a radius gradient ($RG_i$) computed from flow simulation or measurements (e.g., as in 206B and 208B of FIG. 2B), where $$APS_i = RG_{analytic} \cdot \text{Pressure} = \frac{1}{N}\sum_1^N RG_i \cdot \text{Pressure}$$

and $APS_i = RG_{ave} \cdot \text{Pressure}$.

In one embodiment, step 408 may also include outputting the estimates of hemodynamic characteristics to an electronic storage medium (e.g., hard disk, network drive, portable disk, smart phone, tablet etc.) and/or to a display screen. The estimates of the output hemodynamic characteristics may be displayed in greyscale or color in 2D or 3D. The estimates of the hemodynamic characteristics may be overlaid on the geometric model and/or overlaid on an image of the vasculature of interest.

In one embodiment, step 410 may include making the appropriate clinical decision based on the outputted hemodynamic results. In one embodiment, hemodynamic characteristics obtained under a given patient physiological state (e.g., rest, hyperemia, varied levels of stress, etc.) may be used to detect abnormal hemodynamic characteristics. In another embodiment, abnormal levels of hemodynamic characteristics may activate a warning signal that may be generated from a mobile device to notify patients and/or physicians. In another embodiment, the one or more patient-specific parameters and outputted hemodynamic characteristics may be used compute a risk score, where $$\text{Risk score} = f\left(\frac{\text{Stress within the plaque}}{\text{Ultimate Strength of Plaque}}\right) \approx g(APS, APCscore, etc).$$

In yet another embodiment, a cumulative history of biomechanical and/or hemodynamic results may be used to make the appropriate clinical decisions.

FIG. 5 depicts an exemplary method 500 of acquiring a patient-specific geometric model non-invasively (e.g., through coronary computerized tomography angiography (cCTA)), according to an exemplary embodiment of the present disclosure. FIG. 5 may include an exemplary method of performing step 302 of method 300 in FIG. 3, step 402 of method 400 in FIG. 4, and/or the step of non-invasively acquiring a patient-specific geometric model for any one of the embodiments of the present disclosure that includes such a step.

In one embodiment, step 502 may include performing a cardiac CT imaging of a patient in the end diastole phase of a cardiac cycle. In another embodiment, step 502 may include obtaining one or more images of a patient using a non-invasive scanning modality other than a computerized tomography. In another embodiment, step 502 may include obtaining one or more images of a patient during a phase of a cardiac cycle other than the end diastole phase.

In one embodiment, step 504 may include segmenting the one or more cardiac CT images manually or automatically into one or more voxels. In one embodiment, step 506 may include identifying the voxels belonging to the vasculature of interest (e.g., aorta and lumen of the coronary arteries). The segmentation and/or identification may be performed using a processor.

In one embodiment, step 508 may include deriving the patient-specific geometric model from the identified voxels (e.g., using marching cubes). In one embodiment step 508 may also include updating the geometric model based on one or more measured or derived patient-specific parameters, or one or more measured or derived biomechanical and/or hemodynamic characteristics. In one embodiment, step 508 may also include updating the geometric model based on an invasively acquired images of a patient.

FIG. 6 depicts an exemplary method 600 of using patient-specific parameters to output hemodynamic characteristics, using invasive (e.g., IVUS, OCT, motorized pull-back mechanism, etc.) and/or non-invasive (e.g., computational fluid dynamics) measurements, according to an exemplary embodiment of the present disclosure. FIG. 6 may include an exemplary method of performing step 306 of method 300 in FIG. 3 and/or step 408 of method 400 in FIG. 4.

In one embodiment, step 602 may include computing a maximum pressure of a patient from a pulsatile blood pressure. In another embodiment, step 602 may include obtaining the maximum pressure without taking the pulsatile blood pressure of a patient. Step 604 may include computing the pressure change during a cardiac cycle using the maximum pressure obtained in step 602.

In one embodiment, step 606 may include computing the pressure gradient using flow simulation measurements of the pressure change obtained in step 602. For example, a pressure gradient may be computed by utilizing spatial information along a pull-back path using the pressure change. In another embodiment, step 606 may include obtaining the pressure gradient without computing the maximum pressure or pressure change in steps 602 and 604, respectively.

Step 608 may include estimating the wall shear stress ($WSS_i$) using the pressure gradient ($PG_i$) and lumen diameter ($D_i$), where $$WSS_i = PG_i \cdot \frac{D_i}{4}.$$

In one embodiment, other hemodynamic characteristics (e.g., traction) may be computed using the pressure gradient, and lumen characteristics.

In one embodiment, step 610 may include obtaining the radius gradient ($RG_i$) from flow simulations or measurement. The flow simulations or measurements may occur invasively (e.g., using a pull-back path, OCT, IVUS, etc.) or non-invasively (e.g., using cCTA produced images). In one embodiment, the radius gradient may be computed by using 3D geometry constructed from optical coherence tomography or intravascular ultrasound images co-registered to a bi-planar angiogram. In one embodiment, the radius gradient ($RG_i$) may be approximated using radius lengths, $r_1$ and $r_2$, and a lumen length, l, where $RG_i=(r_1-r_2)/l$. In another embodiment, the radius gradient may be computed at a point i ($RG_i$) over interval (ds) for a lumen with a circular area of $A_i$, where $$RG_i = (\sqrt{\frac{A_{i+1}}{\pi}} - \sqrt{\frac{A_i}{\pi}})/ds.$$

In one embodiment, step 612 may include estimating the axial plaque stress value at point i ($APS_i$) using pressure and radius gradient at point i ($RG_i$), where $APS_i=RG_i*$Pressure. The pressure may be obtained from computations of the pressure gradient in step 606. In one embodiment, other hemodynamic characteristics (e.g., fractional flow reserve) may be computed using the pressure gradient, lumen characteristics, and/or radius gradient.

Step 614 may include outputting the hemodynamic characteristics (e.g., wall shear stress and axial plaque stress) onto an electronic storage medium (e.g., hard disk, network drive, portable disk, smart phone, tablet etc.) and/or to a display screen. The estimates of the output hemodynamic characteristics may be displayed in greyscale or color in 2D or 3D. The estimates of the hemodynamic characteristics may be overlaid on the geometric model and/or overlaid on an image of the vasculature of interest.

FIGS. 7, 8, and 9 depict exemplary methods of estimating hemodynamic forces acting on plaque and monitoring risk, using a machine learning algorithm to estimate hemodynamic characteristics, according to an exemplary embodiment of the present disclosure. Moreover, FIG. 7 may include an exemplary method for training a machine learning algorithm for estimating hemodynamic forces, using non-invasive imaging and computational fluid dynamics. The method depicted in FIG. 7 may be used to train a machine learning algorithm that may be applied in the methods depicted in FIG. 8 or 9. While FIG. 8 may include an exemplary method of applying the trained machine learning algorithm using a non-invasively acquired geometric model of a target patient, FIG. 9 may include an exemplary method of applying a trained machine learning algorithm, using an invasively acquired geometric model of a target patient.

FIG. 7 depicts an exemplary method 700 for training a machine learning algorithm for estimating hemodynamic forces, using non-invasive imaging and computational fluid dynamics. In another embodiment, the patient-specific geometric model may be acquired invasively (e.g., through IVUS, OCT, pull-back, pressure wire, etc.), for the purposes of training a machine learning algorithm. In yet another embodiment, step 702 may include receiving a database of geometric models from a plurality of patients for the purpose of training a machine learning algorithm. The acquired geometric model may be represented as a list of points in space (possibly with a list of neighbors for each point) in which the space may be mapped to spatial units between points (e.g., millimeters). The acquired geometric model may be generated by performing one or more cardiac or coronary computerized tomography (cCT) imaging of the patient. The one or more cCT images may be segmented manually or automatically to identify voxels belonging to the aorta and the lumen of the coronary arteries. Once the voxels are identified, the geometric model may be derived (e.g., using marching cubes). In one embodiment, the patient-specific geometric model may include a cardiovascular model of a specific person and/or a patient's ascending aorta and coronary artery tree. In another embodiment, the patient-specific geometric model may be of a vascular model other than the cardiovascular model.

In one embodiment, step 704 may include measuring, deriving, or obtaining patient-specific parameters non-invasively using computational fluid dynamics (CFD). The measured or derived patient-specific parameters may be stored in an electronic storage medium. In one embodiment, the patient-specific parameters may be obtained from a plurality of patients and/or their database of geometric models, for the purpose of training a machine learning algorithm. These patient-specific parameters may include, but are not limited to patient characteristics (e.g., age, gender, etc.), physiological characteristics (e.g., hematocrit level, blood pressure, heart rate, etc.), geometric characteristics (e.g., radius gradient, lumen characteristics, stenosis characteristics, etc.), plaque characteristics (e.g., location of plaque, adverse plaque characteristics score, plaque burden, presence of napkin ring, intensity of plaque, type of plaque, etc.), simplified hemodynamic characteristics (e.g., wall shear stress and axial plaque stress values derived from computational fluid dynamics), and/or coronary dynamics characteristics (e.g., distensibility of coronary artery over cardiac cycle, bifurcation angle change over cardiac cycle, curvature change over cardiac cycle, etc.). Any of the above-mentioned patient-specific parameters may be used to measure or derive other patient-specific parameters. In one embodiment, step 704 may be performed by a processor.

Steps 706A, 706B, 706C, 706D, and 706E depict the measured or derived patient characteristics, physiological characteristics, geometric characteristics, plaque characteristics, and coronary dynamics characteristics, respectively. The patient-specific parameters may be stored in an electronic storage medium.

In one embodiment, step 708 may include outputting one or more simulated hemodynamic characteristics (e.g., axial plaque stress, wall shear stress, etc.), using computational fluid dynamics, for one or more points on the acquired geometric model. In one embodiment, step 708 may be performed by using processors of server systems 106. Step 708 may be performed using the method depicted in FIG. 6.

In one embodiment, step 710 may include associating feature vectors, comprising the measured, derived, or obtained patient-specific parameters, with their corresponding hemodynamic characteristics (e.g., axial plaque stress, wall shear stress, etc.), for one or more points on the geometric model. In one embodiment, step 710 may be performed by using processors of server systems 106.

In one embodiment, step 712 may include using the feature vectors and their associated hemodynamic characteristics to train a machine learning algorithm to predict hemodynamic characteristics. In one embodiment, the feature vectors may be obtained from step 710. The machine learning algorithm may take many forms, including, but not limited to, a multi-layer perceptron, deep learning, support vector machines, random forests, k-nearest neighbors, Bayes networks, etc. Step 712 may be performed using processing devices of server systems 106.

In one embodiment, step 714 may include outputting the trained machine learning algorithm, including feature weights, into an electronic storage medium of server systems 106. The stored feature weights may define the extent to which patient-specific parameters are predictive of hemodynamic characteristics.

FIG. 8 depicts an exemplary method 800 of applying a trained machine learning algorithm to predict hemodynamic characteristics using a non-invasively acquired geometric model of a target patient. The trained machine learning algorithm may be that obtained from method 700 of FIG. 7.

In one embodiment, step 802 may include acquiring a patient-specific geometric model non-invasively (e.g., through coronary computerized tomography angiography). The acquired geometric model may be of the patient for which the hemodynamic characteristics are to be estimated by applying a trained machine learning algorithm. The acquired geometrical model may be represented as a list of points in space (possibly with a list of neighbors for each point) in which the space may be mapped to spatial units between points (e.g., millimeters). The acquired geometric model may be generated by performing one or more cardiac or coronary computerized tomography (cCT) imaging of the patient. The one or more cCT images may be segmented manually or automatically to identify voxels belonging to the aorta and the lumen of the coronary arteries. Once the voxels are identified, the geometric model may be derived (e.g., using marching cubes). In one embodiment, the patient-specific geometric model may include a cardiovascular model of a specific person and/or a patient's ascending aorta and coronary artery tree. In another embodiment, the patient-specific geometric model may be of a vascular model other than the cardiovascular model. The acquired geometric model may be stored in an electronic storage medium of server systems 106.

In one embodiment, step 804 may include measuring, deriving, or obtaining patient-specific parameters non-invasively using computational fluid dynamics (CFD). The measured or derived patient-specific parameters may be stored in an electronic storage medium. The patient-specific parameters may be obtained from the patient for whom the hemodynamic characteristics and/or risk analysis is being sought, or from the patient's geometric model. These patient-specific parameters may include, but are not limited to patient characteristics (e.g., age, gender, etc.), physiological characteristics (e.g., hematocrit level, blood pressure, heart rate, etc.), geometric characteristics (e.g., radius gradient, lumen characteristics, stenosis characteristics, etc.), plaque characteristics (e.g., location of plaque, adverse plaque characteristics score, plaque burden, presence of napkin ring, intensity of plaque, type of plaque, etc.), simplified hemodynamic characteristics (e.g., wall shear stress and axial plaque stress values derived from computational fluid dynamics), and/or coronary dynamics characteristics (e.g., distensibility of coronary artery over cardiac cycle, bifurcation angle change over cardiac cycle, curvature change over cardiac cycle, etc.). Any of the above-mentioned patient-specific parameters may be used to measure or derive other patient-specific parameters. In one embodiment, step 804 may be performed by a processor.

Steps 806A, 806B, 806C, 806D, and 806E depict the measured or derived patient characteristics, physiological characteristics, geometric characteristics, plaque characteristics, and coronary dynamics characteristics, respectively. The patient-specific parameters may be stored in an electronic storage medium.

In one embodiment, step 808 may include applying a trained machine learning algorithm to predict hemodynamic characteristics (e.g., axial plaque stress, wall shear stress, etc.) for one or more points on the geometric model. In one embodiment, step 808 may include using the trained machine learning algorithm obtained from step 714 in method 700, as depicted in FIG. 7. In one embodiment, step 808 may include using the patient-specific parameters obtained from step 804 for one or more points on the patient-specific geometric model when applying the trained machine learning algorithm to predict hemodynamic characteristics for those points. The machine learning algorithm may take many forms, including, but not limited to, a multi-layer perceptron, multivariate regression, deep learning, support vector machines, random forests, k-nearest neighbors, Bayes networks, etc. Step 808 may use processing devices of server systems 106.

In one embodiment, step 810 may include outputting the hemodynamic characteristics (e.g., axial plaque stress, wall shear stress, etc.) and/or results of the machine learning algorithm into an electronic storage medium of server systems 106. The hemodynamic characteristics may be those obtained from the application of a trained machine learning algorithm in step 808. In one embodiment, the output may include patient-specific characteristics other than hemodynamic characteristics. In one embodiment, step 810 may further include monitoring the risk of a patient and/or assessing treatment strategies based on the output.

FIG. 9 may depict an exemplary method 900 of applying a trained machine learning algorithm to predict hemodynamic characteristics using an invasively acquired geometric model of a target patient. The trained machine learning algorithm may be that obtained from method 700 of FIG. 7.

In one embodiment, step 902 may include acquiring a patient-specific geometric model invasively (e.g., through an optical coherence tomography (OCT), intravascular ultrasound (IVUS), pressure wire, etc.). The acquired geometric model may be of the patient for which the hemodynamic characteristics are to be estimated by applying a trained machine learning algorithm. The acquired geometrical model may be represented as a list of points in space (possibly with a list of neighbors for each point) in which the space may be mapped to spatial units between points (e.g., millimeters). Invasive methods for generating the geometric model may include obtaining one or more images by using a pressure wire or by performing intravascular ultrasound (IVUS) imaging or optical coherence tomography (OCT) of the target vasculature. For straight geometries constructed from intravascular imaging, images may be bent or otherwise modified by applying a curvature computed from a co-registered angiogram. Applying the curvature may include first computing the curvature of a vessel from an angiogram and co-registering the optical coherence tomography or intravascular ultrasound-images to the angiogram. The acquired image may then be segmented manually or automatically to identify voxels belonging to the vessels and/or lumen of interest. The segmentation may be performed by a processor. Once the voxels are identified, a geometric model may be derived (e.g., using marching cubes). In one embodiment, the patient-specific geometric model may include a cardiovascular model of a specific person and/or a patient's ascending aorta and coronary artery tree. In another embodiment, the patient-specific geometric model may be of a vascular model other than the cardiovascular model. The acquired geometric model may be stored in an electronic storage medium of server systems 106.

In one embodiment, step 904 may include measuring, deriving, or obtaining patient-specific parameters invasively (e.g., from optical coherence tomography, intravascular ultrasound, pressure-wire, etc.). The measured or derived patient-specific parameters may be stored in an electronic storage medium. The patient-specific parameters may be obtained from the patient for whom the hemodynamic characteristics and/or risk analysis is being sought, or from the patient's geometric model. These patient-specific parameters may include, but are not limited to, patient characteristics (e.g., age, gender, etc.), physiological characteristics (e.g., hematocrit level, blood pressure, heart rate, etc.), geometric characteristics (e.g., radius gradient, lumen characteristics, stenosis characteristics, etc.), plaque characteristics (e.g., location of plaque, adverse plaque characteristics score, plaque burden, presence of napkin ring, intensity of plaque, type of plaque, etc.), simplified hemodynamic characteristics (e.g., wall shear stress and axial plaque stress values derived from computational fluid dynamics), and/or coronary dynamics characteristics (e.g., distensibility of coronary artery over cardiac cycle, bifurcation angle change over cardiac cycle, curvature change over cardiac cycle, etc.). Any of the above-mentioned patient-specific parameters may be used to measure or derive other patient-specific parameters. In one embodiment, step 904 may be performed by a processor.

Steps 906A, 906B, 906C, 906D, and 906E depict the measured, derived, or obtained patient characteristics, physiological characteristics, geometric characteristics, plaque characteristics, and coronary dynamics characteristics, respectively. The list of patient-specific parameters may be the same as the list used in the training mode (e.g., as in method 700). The patient-specific parameters may be stored in an electronic storage medium.

In one embodiment, the list of physiological characteristics 906B may be measured, derived, or obtained using a motorized pull-back system. For example, the pressure along the vessel length may be measured using a pressure wire. The maximum pressure may be computed during a cardiac cycle. In one embodiment, the pressure gradient ($PG_i$) may be computed by using spatial information along one or more pull-back paths, where $$PG_i = \frac{\Delta P_i}{\Delta S_i},$$

with $\Delta P_i$ being a change in pressure and $\Delta S_i$ being a change in spatial metric. Furthermore, noise signals from pressure measurements may be reduced by using filtering techniques (e.g., Kalman filtering).

In one embodiment, the list of geometric characteristics 906C may be measured, derived, or obtained from optical coherence tomography or from intravascular ultrasound images co-registered to an angiogram. These geometric characteristics may include, but are not limited to, the radius gradient, the minimum lumen area and diameter, the degree of stenosis at a lesion, the location of stenotic lesions, the length of stenotic lesions, the irregularity (or circularity) of cross-sectional lumen boundaries, the characteristics of coronary lumen intensity at a lesion, the characteristics of surface of coronary geometry at a lesion, and the characteristics of coronary centerline (e.g., topology) at one or more lesions, etc. In one embodiment, the radius gradient, $RG_i$, may be computed by utilizing 3D geometry constructed from optical coherence tomography or intravascular ultrasound images co-registered to an angiogram, using the formula, $$RG_i = \frac{\Delta R_i}{\Delta S_i},$$

where $\Delta R_i$ is the change in radius and $\Delta S_i$ is an increment of vessel length. Likewise, the minimum lumen area and minimum lumen diameter may be computed from the radius gradient and/or from the 3D geometry constructed from optical coherence tomography or intravascular ultrasound images co-registered to angiogram. The degree of stenosis at a lesion (e.g., percentage diameter/area stenosis) may be computed by determining the virtual reference area profile using Fourier smoothing or kernel regression. The percent stenosis of lesion may be computed using the virtual reference area profile along the vessel centerline. The location of stenotic lesions may be obtained by computing the distance (e.g., parametric arc length of centerline) from the main ostium to the start or center of the lesion. The length of stenotic lesions may be obtained by computing the proximal and distal locations from the stenotic lesion where cross-sectional area may be determined. The characteristics of coronary lumen intensity at a lesion may include the intensity change along the centerline, which may be computed, for example, by using the slope of a linearly-fitted intensity variation. The characteristics of surface of coronary geometry at a lesion may include the 3D surface curvature of geometry (e.g., Gaussian, maximum, minimum, mean, etc.). The characteristics of coronary centerline (e.g., topology) at one or more lesions may include the curvature (bending) of coronary centerline and/or the tortuosity (non-planarity) of the coronary centerline. The curvature (bending) of coronary centerline may be obtained by computing the Frenet curvature, $\kappa$, in the formula $$\kappa = \frac{|p' \times p''|}{|p'|^3},$$

where p may be a coordinate of centerline parameterized by cumulative arc-length to the starting point, and/or by computing an inverse of the radius of a circumscribed circle along the centerline points. The tortuosity (non-planarity) of the coronary centerline may be obtained by computing the Frenet torsion, $\sigma$, in the formula, $$\tau = \frac{(p' \times p'') \cdot p'''}{|p' \times p''|^2},$$

where p may be a coordinate of a centerline.

In one embodiment, the plaque characteristics 906D may be measured, derived, or obtained using coronary CT angiography, intravascular ultrasound, near-infrared spectroscopy, and/or optical coherence tomography. The plaque characteristics may include, but are not limited to the location of plaque along the centerline of the vessel, the plaque burden (e.g., cap thickness, wall thickness, area, volume, etc.), the presence of a Napkin ring, the intensity of plaque, the type of plaque (e.g., calcified, non-calcified, etc.), the distance from the plaque location to the ostium, the distance from the plaque location to the nearest downstream or upstream bifurcation, and/or an adverse plaque characteristics (APC) score.

In one embodiment, the adverse plaque characteristics score (APC score) may be computed based on the presence of positive remodeling, presence of a low attenuation plaque, and/or presence of spotty intra-plaque calcification. Determining the presence of positive remodeling may include determining a diseased segment based on the degree of stenosis or the presence of plaque in the wall segmentation. A positive remodeling index may be computed by evaluating a cross-sectional area (CSA) of a vessel (EEM) at a lesion and reference segments based on the following equation:

$$\text{positive remodeling index} = \frac{CSA \text{ of } EEM \text{ at lesion}}{CSA \text{ of } EEM \text{ at reference}}.$$

If the positive remodeling index is greater than 1.05, the presence of a positive remodeling and/or the positive remodeling index may be reported. Determining the presence of low attenuation plaque may include detecting non-calcified plaques in wall segmentation at a diseased segment. If a region of non-calcified plaque has an intensity of less than or equal to 30 Hounsfield Units (HU), the presence of low attenuation plaque and/or the volume of non-calcified plaque may be reported. In some embodiments, the presence of low attenuation plaque and/or the volume of non-calcified plaque may be reported even if a region of non-calcified plaque has an intensity of less than or equal to 50 Hounsfield Units (HU). Determining the presence of spotty and/or blob-shaped intra-plaque calcification may include detecting calcified plaques in wall segmentation at a diseased segment. A Hessian-based eigenvalue analysis may be utilized to detect blob-shaped calcified plaques. If the diameter of intra-lesion nodular calcified plaque is less than 3 mm, the presence of spotty and/or blob-shaped calcification and/or the diameter of the plaque may be reported.

In one embodiment, the coronary dynamics characteristics 906E may be measured, derived, or obtained from multi-phase coronary computed tomography angiography (e.g., diastole and systole) or derived from an analysis of a cine-angiogram. The coronary dynamics characteristics may include, but are not limited to, the distensibility of a coronary artery over the cardiac cycle, the bifurcation angle change over the cardiac cycle, and/or the curvature change over the cardiac cycle.

In one embodiment, step 908 may include applying a trained machine learning algorithm to predict biomechanical and/or hemodynamic characteristics (e.g., axial plaque stress, wall shear stress, radius gradient, etc.) for points on the target patient's geometric model. In one embodiment, step 908 may include using the trained machine learning algorithm obtained from step 714 in method 700, as depicted in FIG. 7. In one embodiment, step 908 may include using the patient-specific parameters obtained from step 904 for one or more points on the patient-specific geometric model when applying the trained machine learning algorithm to predict hemodynamic characteristics for those points. The machine learning algorithm may take many forms, including, but not limited to, a multi-layer perceptron, multivariate regression, deep learning, support vector machines, random forests, k-nearest neighbors, Bayes networks, etc. Step 908 may use processing devices of server systems 106.

In one embodiment, step 910 may include outputting the hemodynamic characteristics (e.g., axial plaque stress, wall shear stress, etc.) and/or results of the machine learning algorithm into an electronic storage medium of server systems 106. The hemodynamic characteristics may be those obtained from the application of a trained machine learning algorithm in step 908. In one embodiment, the output may include patient-specific characteristics other than hemodynamic characteristics. In one embodiment, step 910 may further include monitoring the risk of a patient and/or assessing treatment strategies based on the output.

Alternatively, or in addition to steps 808 and 908 of methods 800 and 900, respectively, biomechanical and/or hemodynamic characteristics may be predicted, computed, or derived from the patient-specific parameters using computational flow dynamics and/or Hagen-Poiseuille assumptions. For example, the wall shear stress may be derived by computing the cross-sectional area at a point i ($A_i$) on a vasculature or geometric model, computing the effective lumen diameter ($D_i$), where $$D_i = 2\sqrt{\frac{A_i}{\pi}},$$

and estimating the wall shear stress at the point i ($WSS_i$) using a pressure gradient ($PG_i$) computed from a flow simulation or measurements, where $$WSS_i = PG_i \cdot \frac{D_i}{4}.$$

In another example, the axial plaque stress may be derived by computing the radius gradient at a point i ($RG_i$) over an interval (ds), where $$RG_i = \left(\sqrt{\frac{A_{i+1}}{\pi}} - \sqrt{\frac{A_i}{\pi}}\right)\bigg/ ds,$$

and estimating the axial plaque stress over a point i, $APS_i$ using a radius gradient ($RG_i$) computed from flow simulation or measurements (e.g., as in 206B and 208B of FIG. 2B), where $$APS_i = RG_{analytic} \cdot \text{Pressure} = \frac{1}{N}\sum_1^N RG_i \cdot \text{Pressure}$$

and $APS_i = RG_{ave} \cdot \text{Pressure}$. In one embodiment, the simplified hemodynamic characteristics may be used to compute more accurate hemodynamic characteristics and/or be used as part of a machine learning algorithm to obtain the hemodynamic characteristics for points on the geometric model where the simplified hemodynamic characteristics may not be known.

Figure 10:
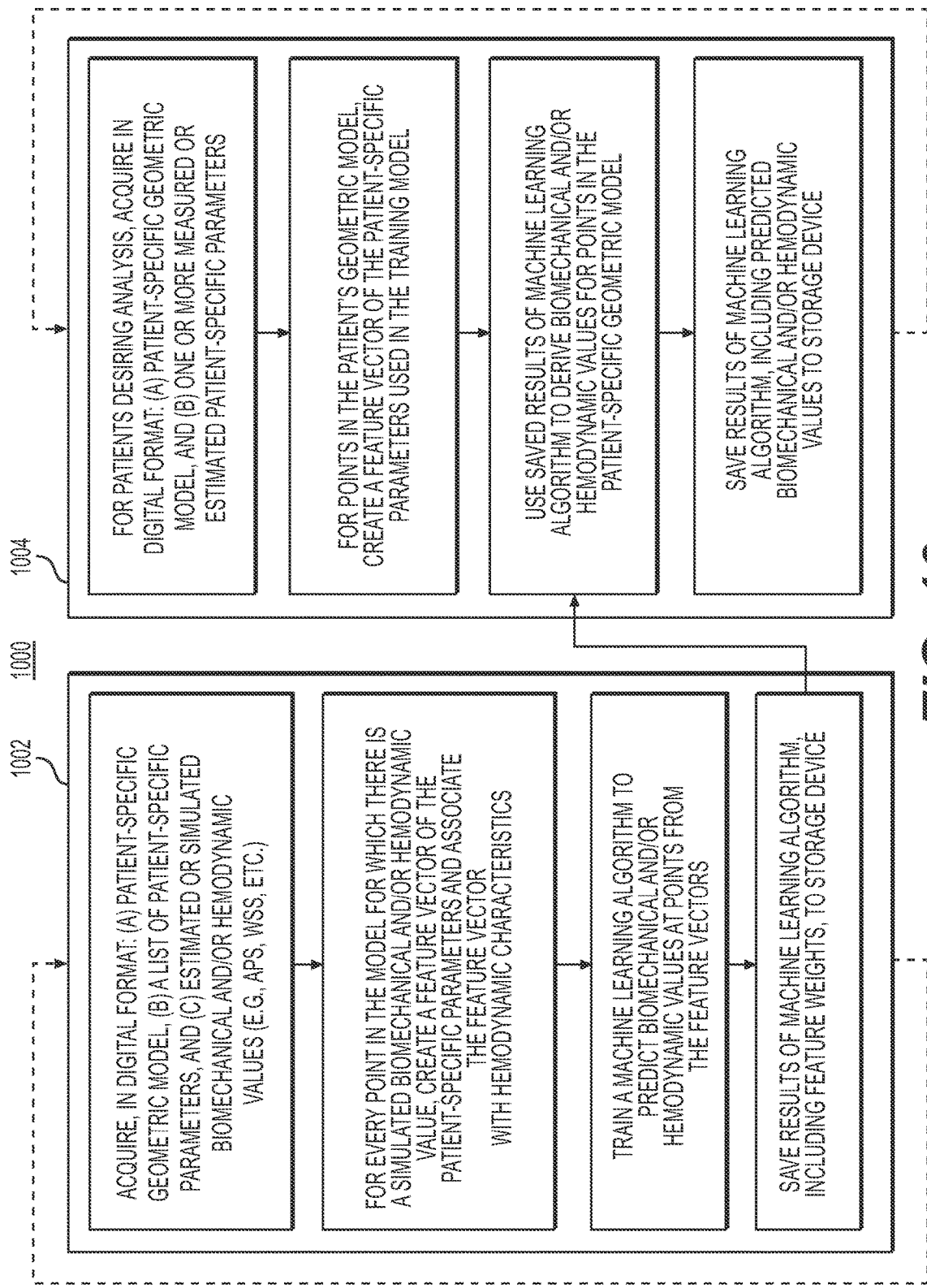
FIG. 10 is a block diagram of an exemplary method of training and applying a machine learning algorithm using patient-specific parameters to output values of hemodynamic forces, according to an exemplary embodiment of the present disclosure.

FIG. 10 is a block diagram of an exemplary method for estimating biomechanical and/or hemodynamic values on one or more points of a patient-specific geometric model using one or more patient-specific parameters, according to an exemplary embodiment of the present disclosure. These patient-specific parameters may include, but are not limited to patient characteristics (e.g., age, gender, etc.), physiological characteristics (e.g., hematocrit level, blood pressure, heart rate, etc.), geometric characteristics (e.g., radius gradient, lumen characteristics, stenosis characteristics, etc.), plaque characteristics (e.g., location of plaque, adverse plaque characteristics score, plaque burden, presence of napkin ring, intensity of plaque, type of plaque, etc.), simplified hemodynamic characteristics (e.g., wall shear stress and axial plaque stress values derived from computational fluid dynamics), and/or coronary dynamics characteristics (e.g., distensibility of coronary artery over cardiac cycle, bifurcation angle change over cardiac cycle, curvature change over cardiac cycle, etc.). The method 1000 of FIG. 10 may be performed by server systems 106, based on information received from physicians 102 and/or third party providers 104 over electronic network 100.

In one embodiment, the method 1000 of FIG. 10 may include a training method 1002, for training one or more machine learning algorithms based on patient-specific parameters from numerous patients and measured, estimated, and/or simulated biomechanical and/or hemodynamic values, and a production method 1004 for using the machine learning algorithm results to predict a target patient's biomechanical and/or hemodynamic characteristics.

In one embodiment, training method 1002 may involve acquiring, for each of a plurality of individuals, e.g., in digital format: (a) a patient-specific geometric model, (b) one or more measured or estimated patient-specific parameters, and (c) estimated or simulated biomechanical and/or hemodynamic values (e.g., axial plaque stress, wall shear stress, radius gradient, etc.). Training method 1002 may then involve, for one or more points in each patient's model, creating a feature vector of the patients' physiological parameters at one or more points of a geometric model and associating the feature vector with the values of hemodynamic characteristics at those points of the geometric model. Training method 1002 may then save the results of the machine learning algorithm, including feature weights, in a storage device of server systems 106. The stored feature weights may define the extent to which patient-specific parameters and/or anatomical geometry are predictive of hemodynamic characteristics.

In one embodiment, the production method 1004 may involve estimating biomechanical and/or hemodynamic characteristics for a particular patient, based on results of executing training method 1002. In one embodiment, production method 1004 may include acquiring, e.g. in digital format: (a) a patient-specific geometric model, and (b) one or more measured or estimated patient-specific parameters (e.g., patient characteristics, physiological characteristics, geometric characteristics, plaque characteristics, simplified hemodynamic characteristics, and/or coronary dynamics characteristics). For multiple points in the patient's geometric model, production method 1004 may involve creating a feature vector of the patient-specific parameters used in the training mode. Production method 1004 may then use saved results of the machine learning algorithm to produce estimates of the patient's biomechanical and/or hemodynamic characteristics for each point in the patient-specific geometric model. Finally, production method 1004 may include saving the results of the machine learning algorithm, including predicted biomechanical and/or hemodynamic characteristics, to a storage device of server systems 106.

FIGS. 11A and 11B are block diagrams of exemplary methods, 1100A and 1100B, respectively, for using hemodynamic characteristics to monitor risk and make appropriate clinical decisions, according to an exemplary embodiment of the present disclosure. Moreover, FIGS. 11A-11B depict embodiments for performing step 308 of making appropriate clinical decisions based on the saved hemodynamic characteristics.

Specifically, FIG. 11A depicts a block diagram of method 1100A for using hemodynamic characteristics to monitor risk and make appropriate clinical decisions in a catheterization laboratory. In one embodiment, step 1102A may include determining whether the fractional flow reserve (FFR) value of the patient is less than or equal to a threshold for fractional flow reserve values (e.g., 0.8). The fractional flow reserve of the patient may be obtained, measured, or derived from the electronic storage medium and/or by using the embodiments disclosed in the present disclosure, which provide systems and methods for estimating biomechanical and/or hemodynamic characteristics, including fractional flow reserve, using patient-specific parameters.

If, subsequent to step 1102A, the fractional flow reserve (FFR) value of the patient is less than or equal to the threshold for fractional flow reserve values, e.g., 0.8, then step 1104A may include determining whether the stress within a plaque is greater than an ultimate plaque strength divided by a safety factor (e.g., of two) or whether the axial plaque stress multiplied by the adverse plaque characteristics (APC) score is greater than or equal to a threshold for the product value (e.g., 40,000). If, subsequent to step 1102A, the fractional flow reserve (FFR) value of the patient is greater than the threshold for fractional flow reserve values (e.g., 0.8), then step 1106A may also include determining whether the stress within a plaque is greater than an ultimate plaque strength divided by a safety factor (e.g., of two) or whether the axial plaque stress multiplied by the adverse plaque characteristics (APC) score is greater than or equal to a threshold for the product value, e.g., 40,000.

The adverse plaque characteristics (APC) score can be calculated by converting measurements of APC (e.g., presence of positive remodeling, napkin ring sign, low Hounsfield unit, or spotty calcification) to ordinal variables (e.g., 1, 2, 3, etc.) based on the number of observed types of APC or continuous variables (e.g., probability) derived from machine-learning based classifier (e.g., logistic regression, support vector machine, etc.). In some embodiments, the adverse plaque characteristics may include, for example, atherosclerotic plaque characteristics.

If, subsequent to steps 1102A and 1104A, the fractional flow reserve (FFR) is less than or equal to the threshold for fractional flow reserve values (e.g., 0.8) and either the stress within a plaque is greater than an ultimate plaque strength divided by a safety factor (e.g., of two) or the axial plaque stress (APS) multiplied by the adverse plaque characteristics (APC) score is greater than or equal to the threshold for the product value (e.g., 40,000), then step 1108A may include performing a percutaneous coronary intervention (PCI) on the patient. If, subsequent to steps 1102A and 1104A, the fractional flow reserve (FFR) is less than or equal to the threshold for the fractional flow reserve value (e.g., 0.8), but neither the stress within a plaque is greater than an ultimate plaque strength divided by a safety factor (e.g. 2) nor is the axial plaque stress (APS) multiplied by the adverse plaque characteristics (APC) score greater than or equal to the threshold for the product value (e.g., 40,000), then step 1110A may include performing a percutaneous coronary intervention (PCI) on the patient or a close medical follow-up with a strict risk control.

If, subsequent to steps 1102A and 1106A, the fractional flow reserve (FFR) is greater than the threshold for the fractional flow reserve value (e.g., 0.8) and either the stress within a plaque is greater than an ultimate plaque strength divided by a safety factor (e.g. 2) or the axial plaque stress (APS) multiplied by the adverse plaque characteristics (APC) score is greater than or equal to the threshold for the product value (e.g., 40,000), then step 1112A may include performing a percutaneous coronary intervention (PCI) on the patient or a close medical follow-up with a strict risk control. If, subsequent to steps 1102A and 1106A, the fractional flow reserve (FFR) is greater than the threshold for the fractional flow reserve value 0.8, but neither the stress within a plaque is greater than an ultimate plaque strength divided by a safety factor (e.g., 2) nor is the axial plaque stress (APS) multiplied by the adverse plaque characteristics (APC) score greater than or equal to the threshold for the product value (e.g., 40,000), then step 1114A may include performing a medical treatment.

FIG. 11B depicts a block diagram of method 1100B for using hemodynamic characteristics to monitor risk and make appropriate clinical decisions in an outpatient clinic. In one embodiment, step 1102B may include determining whether a stenosis within the acquired image of a patient (e.g., cCTA) is more than 50%. Information about the stenosis of the patient may be obtained, measured, or derived from the electronic storage medium and/or by using the embodiments disclosed in the present disclosure, which provide systems and methods for estimating biomechanical and/or hemodynamic characteristics using patient-specific parameters.

If, subsequent to step 1102B, the stenosis within the acquired image of a patient is more than 50%, then step 1104B may include determining whether the stress within a plaque is greater than an ultimate plaque strength divided by a safety factor (e.g., of two) or whether the axial plaque stress multiplied by the adverse plaque characteristics (APC) score greater than or equal to a threshold for the product value (e.g., 40,000). If, subsequent to step 1102B, the stenosis within the acquired image of a patient is less than 50%, then step 1106B may also include determining whether the stress within a plaque is greater than an ultimate plaque strength divided by a safety factor of two or whether the axial plaque stress multiplied by the adverse plaque characteristics (APC) score is greater than or equal to a threshold for the product value (e.g., 40,000).

If, subsequent to steps 1102B and 1104B, the stenosis within the acquired image of a patient is more than 50% and either the stress within a plaque is greater than an ultimate plaque strength divided by a safety factor (e.g. of two) or the axial plaque stress (APS) multiplied by the adverse plaque characteristics (APC) score is greater than or equal to the threshold for the product value (e.g., 40,000), then step 1108B may include performing an invasive procedure on the patient. If, subsequent to steps 1102B and 1104B, the stenosis within the acquired image of a patient is more than 50%, but neither the stress within a plaque is greater than an ultimate plaque strength divided by a safety factor (e.g. of two) nor is the axial plaque stress (APS) multiplied by the adverse plaque characteristics (APC) score greater than or equal to the threshold for the product value (e.g., 40,000), then step 1110B may include performing an invasive procedure on the patient and/or performing a close medical follow-up with a strict risk control.

If, subsequent to steps 1102B and 1106B, the stenosis within the acquired image of a patient is less than 50% and either the stress within a plaque is greater than an ultimate plaque strength divided by a safety factor (e.g. two) or the axial plaque stress (APS) multiplied by the adverse plaque characteristics (APC) score is greater than or equal to the threshold for the product value (e.g., 40,000), then step 1112B may include performing a close medical follow-up with a strict risk control on the patient. If, subsequent to steps 1102B and 1106B, the stenosis within the acquired image of a patient is less than 50%, but neither the stress within a plaque is greater than an ultimate plaque strength divided by a safety factor (e.g. 2) nor is the axial plaque stress (APS) multiplied by the adverse plaque characteristics (APC) score greater than or equal to the threshold for the product value (e.g., 40,000), then step 1114B may include performing a medical treatment.

FIG. 12 depicts an exemplary method 1200 for determining an exercise intensity using hemodynamic characteristics based on a simulated or performed exercise and/or stress test, according to an exemplary embodiment of the present disclosure.

In one embodiment, step 1202 may include acquiring a patient-specific geometric model invasively (e.g., OCT, IVUS, etc.) and/or non-invasively (e.g., cCTA). The acquired geometric model may include one or more target vessels and/or tissues of a patient and may be saved as a digital representation in an electronic storage medium. Non-invasive methods for generating the geometric model may include performing a cardiac CT imaging of the patient. Invasive methods for generating the geometric model may include performing intravascular ultrasound (IVUS) imaging or optical coherence tomography (OCT) of the target vasculature. The invasively and/or non-invasively acquired image may then be segmented manually or automatically to identify voxels belonging to the vessels and/or lumen of interest. Once the voxels are identified, a geometric model may be derived (e.g., using marching cubes). In one embodiment, the patient-specific geometric model may include a cardiovascular model of a specific person and/or a patient's ascending aorta and coronary artery tree. In another embodiment, the patient-specific geometric model may be of a vascular model other than the cardiovascular model. In one embodiment, the geometric model may be represented as a list of points in space (possibly with a list of neighbors for each point) in which the space may be mapped to spatial units between points (e.g., millimeters).

Step 1204 may include performing and/or simulating an exercise test (e.g., treadmill test) on the patient. In one embodiment, an exercise test is any aerobic physical exercise that places a patient in a stressed physiological condition (e.g., raised heart beat) for a sustained period (e.g., more than 5 minutes).

Step 1206 may include obtaining a patient's maximum physiological characteristics (e.g., hematocrit level, blood pressure, heart rate, etc.) non-invasively using a mobile device. In one embodiment, a patient's maximum physiological characteristics may be obtained when a patient is under a stressed physiological condition, for example, when the patient is undergoing the exercise test or immediately thereafter. The physiological characteristics may include, but is not limited to, the blood pressure, heart rate, hematocrit level, and/or any physiological measurement or derivation that may be obtained non-invasively, using a mobile device.

Step 1208A, 1208B, 1208C, 1208D, and 1208E may include obtaining, measuring, or deriving patient-specific parameters (e.g., geometric characteristics, plaque characteristics, coronary dynamic characteristics, patient characteristics, physiological characteristics, etc.). While the geometric characteristics, plaque characteristics, and/or coronary dynamics characteristics may be pre-acquired from literature, patient history, and/or the electronic storage medium, the patient characteristics and physiological characteristics may be obtained by input and/or extracted from step 1206.

In one embodiment, step 1210 may include determining the biophysical and/or hemodynamic characteristics (e.g., axial plaque stress, wall shear stress, etc.) using computational fluid dynamics and/or a machine learning algorithm. In one embodiment, the simplified hemodynamics characteristics (e.g., wall shear stress, axial plaque stress, etc.) may be derived from Hagen-Poiseuille flow assumptions. For example, the wall shear stress may be derived by computing the cross-sectional area at a point i ($A_i$) on a vasculature, computing the effective lumen diameter ($D_i$), where $$D_i = 2\sqrt{\frac{A_i}{\pi}},$$

and estimating the wall shear stress at the point i ($WSS_i$) using a pressure gradient ($PG_i$) computed from a flow simulation or measurements, where $$WSS_i = PG_i \cdot \frac{D_i}{4}.$$

In another example, the axial plaque stress may be derived by computing the radius gradient at a point i ($RG_i$) over an interval (ds), where $$RG_i = \left(\sqrt{\frac{A_{i+1}}{\pi}} - \sqrt{\frac{A_i}{\pi}}\right)/ds,$$

and estimating APS ($APS_i$) using a radius gradient ($RG_i$) computed from flow simulation or measurements (e.g., as in 206B and 208B of FIG. 2B), where $$APS_i = RG_{analytic} \cdot \text{Pressure} = \frac{1}{N}\sum_1^N RG_i \cdot \text{Pressure}$$

and $APS_i = RG_{ave} \cdot \text{Pressure}$. In one embodiment, the simplified hemodynamic characteristics may be used to compute more accurate hemodynamic characteristics and/or be used as part of a machine learning algorithm to obtain the hemodynamic characteristics for points on the geometric model where the simplified hemodynamic characteristics may not be known.

In one embodiment, step 1210 may include using the patient-specific parameters obtained from step 1208A-E (e.g., patient characteristics, physiological characteristics, geometric characteristics, plaque characteristics, simplified hemodynamic characteristics, and/or coronary dynamics characteristics) to form feature vectors to train and apply machine learning algorithm to determine the maximum allowable biomechanical and/or hemodynamic characteristics. For example, for one or more points on the geometric model where a simplified maximum allowable hemodynamic characteristics can be calculated using computational fluid dynamics, a feature vector may then be associated with the computed maximum allowable hemodynamic characteristics for the one or more points on the geometric model. The feature vectors and their associated maximum allowable biomechanical and/or hemodynamic characteristics may be used to train a machine learning algorithm that may be stored in an electronic storage medium. The trained machine learning algorithm may be applied to another geometric model using another set of patient-specific parameters to derive the maximum allowable biomechanical and/or hemodynamic characteristics for points on the geometric model.

In one embodiment, step 1212 may include outputting the maximum allowable biomechanical and/or hemodynamic characteristics to an electronic storage medium and/or display of server systems 106. The hemodynamic characteristics may be those obtained from the application of a trained machine learning algorithm in step 1210. In one embodiment, the output may include patient-specific characteristics other than the maximum allowable hemodynamic characteristics.

In one embodiment, step 1214 may include producing a warning in response to abnormal values of hemodynamic characteristics (e.g., axial plaque stress, wall shear stress, etc.). In one embodiment, the hemodynamic characteristics may be measured, derived, or obtained using the method 1300 depicted in FIG. 13, and may be compared to the maximum allowable hemodynamic characteristics that may be measured, derived or obtained using method 1200 depicted in FIG. 12.

FIG. 13 is a block diagram of exemplary method 1300 for using predetermined exercise intensity (e.g., as in FIG. 12) to monitor risk in patients, according to an exemplary embodiment of the present disclosure.

In one embodiment, step 1302 may include acquiring a patient-specific geometric model invasively (e.g., OCT, IVUS, etc.) and/or non-invasively (e.g., cCTA). The geometric model may be the same as the geometric model acquired to determine the maximum allowable hemodynamic characteristics for the same patient. The acquired geometric model may include one or more target vessels and/or tissues of a patient and may be saved as a digital representation in an electronic storage medium. Non-invasive methods for generating the geometric model may include performing a cardiac CT imaging of the patient. Invasive methods for generating the geometric model may include performing intravascular ultrasound (IVUS) imaging or optical coherence tomography (OCT) of the target vasculature. The invasively and/or non-invasively acquired image may then be segmented manually or automatically to identify voxels belonging to the vessels and/or lumen of interest. Once the voxels are identified, a geometric model may be derived (e.g., using marching cubes). In one embodiment, the patient-specific geometric model may include a cardiovascular model of a specific person and/or a patient's ascending aorta and coronary artery tree. In another embodiment, the patient-specific geometric model may be of a vascular model other than the cardiovascular model. In one embodiment, the geometric model may be represented as a list of points in space (possibly with a list of neighbors for each point) in which the space may be mapped to spatial units between points (e.g., millimeters).

Step 1304 may include obtaining a patient's physiological and/or blood supply characteristics (e.g., hematocrit level, blood pressure, heart rate, etc.) using a mobile device. The physiological characteristics may include, but is not limited to, the blood pressure, heart rate, hematocrit level, and/or any physiological measurement or derivation that may be obtained non-invasively, using a mobile device.

Step 1306A, 1306B, 1306C, 1306D, and 1306E may include obtaining, measuring, or deriving patient-specific parameters (e.g., geometric characteristics, plaque characteristics, coronary dynamic characteristics, patient characteristics, physiological characteristics, etc.). While the geometric characteristics, plaque characteristics, and/or coronary dynamics characteristics may be pre-acquired from literature, patient history, and/or the electronic storage medium, the patient characteristics and physiological characteristics may be obtained by input and/or extracted from step 1304, using a mobile device.

In one embodiment, step 1308 may include determining the patient's current biophysical and/or hemodynamic characteristics (e.g., axial plaque stress, wall shear stress, etc.) using computational fluid dynamics and/or a machine learning algorithm.

In one embodiment, the simplified hemodynamics characteristics (e.g., wall shear stress, axial plaque stress, etc.) may be derived from Hagen-Poiseuille flow assumptions. For example, the wall shear stress may be derived by computing the cross-sectional area at a point i ($A_i$) on a vasculature, computing the effective lumen diameter ($D_i$), where $$D_i = 2\sqrt{\frac{A_i}{\pi}},$$

and estimating the wall shear stress at the point i ($WSS_i$) using a pressure gradient ($PG_i$) computed from a flow simulation or measurements, where $$WSS_i = PG_i \cdot \frac{D_i}{4}.$$

In another example, the axial plaque stress may be derived by computing the radius gradient at a point i ($RG_i$) over an interval (ds), where $$RG_i = \left(\sqrt{\frac{A_{i+1}}{\pi}} - \sqrt{\frac{A_i}{\pi}}\right)/ds,$$

and estimating APS ($APS_i$) using a radius gradient ($RG_i$) computed from flow simulation or measurements (e.g., as in 206B and 208B of FIG. 2B), where $$APS_i = RG_{analytic} \cdot \text{Pressure} = \frac{1}{N}\sum_1^N RG_i \cdot \text{Pressure}$$

and $APS_i = RG_{ave} \cdot \text{Pressure}$. In one embodiment, the simplified hemodynamic characteristics may be used to compute more accurate hemodynamic characteristics and/or be used as part of a machine learning algorithm to obtain the hemodynamic characteristics for points on the geometric model where the simplified hemodynamic characteristics may not be known.

In one embodiment, step 1308 may include using the patient-specific parameters obtained from step 1208A-E (e.g., patient characteristics, physiological characteristics, geometric characteristics, plaque characteristics, simplified hemodynamic characteristics, and/or coronary dynamics characteristics) to form feature vectors to train and apply machine learning algorithm to determine the current biomechanical and/or hemodynamic characteristics of the patient. For example, for one or more points on the geometric model where a simplified hemodynamic characteristics can be calculated using computational fluid dynamics, a feature vector may then be associated with the computed hemodynamic characteristics for the one or more points on the geometric model. The feature vectors and their associated biomechanical and/or hemodynamic characteristics may be used to train a machine learning algorithm that may be stored in an electronic storage medium. The trained machine learning algorithm may be applied to another geometric model using another set of patient-specific parameters to derive the biomechanical and/or hemodynamic characteristics for points on the geometric model.

Step 1310 may include obtaining the patient's maximum allowable hemodynamic characteristics. In one embodiment, a patient's maximum physiological characteristics may be obtained from prior tests and/or from method 1200 depicted in FIG. 12, while a patient is undergoing the exercise test or immediately after an exercise test. In other embodiments, a patient's maximum physiological characteristics may be simulated and/or obtained from literature (e.g., a patient's medical records). A patient's maximum physiological characteristics may be obtained from or stored in an electronic storage system of server system 106.

In one embodiment, step 1312 may include comparing the current hemodynamic characteristics of a patient with the maximum allowable hemodynamic characteristics of a patient. In one embodiment, the comparison may involve determining whether the current hemodynamic characteristics is greater than, less than, or within an optimal range below the maximum allowable hemodynamic characteristics.

In one embodiment, step 1314 may include producing a warning in response to abnormal values of hemodynamic characteristics. For example, if the current measured, derived, or obtained axial plaque stress is above an optimal range or value for the maximum allowable hemodynamic characteristic, a warning may be provided to the patient or physician. In one embodiment, the warning may be a signal or prompt provided on the mobile device of the patient or physician. In one embodiment, a cumulative history of the measurements or estimations of the hemodynamic characteristics of a patient and/or a cumulative history of whether these measurements or estimations were abnormal and/or above an optimal range of the maximum allowable hemodynamic characteristic may be saved to an electronic storage medium of server system 106.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for training a machine learning algorithm comprising:
   acquiring a plurality of patient-specific geometric models;
   determining at least one patient-specific parameter associated with each of the plurality of patient-specific geometric models;
   determine at least one simulated hemodynamic characteristic for one or more points of the plurality of patient-specific geometric models;
   for each of the plurality of patient-specific geometric models, associating the at least one patient-specific parameter with the at least one simulated hemodynamic characteristic;
   using the association of the at least one patient-specific parameter with the at least one simulated hemodynamic characteristic, training a machine learning algorithm; and
   outputting the trained machine learning algorithm.

2. The computer-implemented method of claim 1, wherein the at least one simulated hemodynamic characteristic includes a wall shear stress and/or an axial plaque stress.

3. The computer-implemented method of claim 1, wherein the at least one patient-specific parameter includes at least one of a patient characteristic, a physiological characteristic, a geometric characteristic, a plaque characteristic, or a coronary dynamics characteristic.

4. The computer-implemented method of claim 3, wherein the at least one patient-specific parameter includes a pressure gradient.

5. The computer-implemented method of claim 1, wherein determining the at least one simulated hemodynamic characteristic includes using computational fluid dynamics.

6. The computer-implemented method of claim 1, wherein associating the at least one patient-specific parameter with the at least one simulated hemodynamic characteristic includes associating a feature vector of a plurality of patient-specific parameters with the at least one simulated hemodynamic characteristic.

7. The computer-implemented method of claim 6, wherein the feature vectors are used to train the machine learning algorithm.

8. The computer-implemented method of claim 1, wherein the at least one patient-specific parameter is obtained non-invasively.

9. The computer-implemented method of claim 1, wherein the trained machine learning algorithm includes at least one feature weight.

10. A system for monitoring hemodynamic risk in a patient, the system comprising:
    at least one memory storing instructions; and
    at least one processor operatively connected to the at least one memory and configured to execute the instructions to perform operations, including:
      acquiring a plurality of patient-specific geometric models;
      determining at least one patient-specific parameter associated with each of the plurality of patient-specific geometric models;
      determine at least one simulated hemodynamic characteristic for one or more points of the plurality of patient-specific geometric models;
      for each of the plurality of patient-specific geometric models, associating the at least one patient-specific parameter with the at least one simulated hemodynamic characteristic;
      using the association of the at least one patient-specific parameter with the at least one simulated hemodynamic characteristic, training a machine learning algorithm; and
      outputting the trained machine learning algorithm.

11. The system of claim 10, wherein the at least one simulated hemodynamic characteristic includes a wall shear stress and/or an axial plaque stress.

12. The system of claim 10, wherein the at least one patient-specific parameter includes at least one of a patient characteristic, a physiological characteristic, a geometric characteristic, a plaque characteristic, or a coronary dynamics characteristic.

13. The system of claim 10, wherein the at least one patient-specific parameter includes a pressure gradient.

14. The system of claim 10, wherein the at least one patient-specific parameter includes at least one of a patient characteristic, a physiological characteristic, a geometric characteristic, a plaque characteristic, or a coronary dynamics characteristic.

15. The system of claim 10, wherein the at least one patient-specific parameter is obtained non-invasively.

16. A non-transitory computer readable medium for use on a computer system containing computer-executable programming instructions for a method of monitoring hemodynamic risk in a patient, the method comprising:
- acquiring a plurality of patient-specific geometric models;
- determining at least one patient-specific parameter associated with each of the plurality of patient-specific geometric models;
- determine at least one simulated hemodynamic characteristic for one or more points of the plurality of patient-specific geometric models;
- for each of the plurality of patient-specific geometric models, associating the at least one patient-specific parameter with the at least one simulated hemodynamic characteristic;
- using the association of the at least one patient-specific parameter with the at least one simulated hemodynamic characteristic, training a machine learning algorithm; and
- outputting the trained machine learning algorithm.

17. The non-transitory computer readable medium of claim 16, wherein the at least one simulated hemodynamic characteristic includes a wall shear stress and/or an axial plaque stress.

18. The non-transitory computer readable medium of claim 16, wherein the at least one patient-specific parameter includes at least one of a patient characteristic, a physiological characteristic, a geometric characteristic, a plaque characteristic, or a coronary dynamics characteristic.

19. The non-transitory computer readable medium of claim 16, wherein the at least one patient-specific parameter includes a pressure gradient.

20. The non-transitory computer readable medium of claim 16, wherein the at least one patient-specific parameter includes at least one of a patient characteristic, a physiological characteristic, a geometric characteristic, a plaque characteristic, or a coronary dynamics characteristic.

* * * * *